United States Patent
Jin

(10) Patent No.: US 10,428,136 B2
(45) Date of Patent: Oct. 1, 2019

(54) I DOMAIN CHIMERIC ANTIGEN RECEPTOR SPECIFIC TO ICAM-1

(71) Applicant: Cornell University, Ithaca, NY (US)

(72) Inventor: Moonsoo Jin, New York, NY (US)

(73) Assignee: Cornell University, Center for Technology Licensing ("CTL"), Ithaca, NY (US)

( * ) Notice: Subject to any disclaimer, the term of this patent is extended or adjusted under 35 U.S.C. 154(b) by 182 days.

(21) Appl. No.: 15/675,508

(22) Filed: Aug. 11, 2017

(65) Prior Publication Data

US 2018/0066035 A1 Mar. 8, 2018

Related U.S. Application Data

(60) Provisional application No. 62/383,139, filed on Sep. 2, 2016, provisional application No. 62/419,817, filed on Nov. 9, 2016.

(51) Int. Cl.

| C07K 14/705 | (2006.01) |
|---|---|
| C07K 14/72 | (2006.01) |
| A61K 39/00 | (2006.01) |
| A61K 51/08 | (2006.01) |
| A61K 35/17 | (2015.01) |
| C07K 14/725 | (2006.01) |
| C12N 5/0783 | (2010.01) |
| A61K 38/17 | (2006.01) |

(52) U.S. Cl.
CPC ............ *C07K 14/723* (2013.01); *A61K 35/17* (2013.01); *A61K 38/1796* (2013.01); *A61K 39/0011* (2013.01); *A61K 51/083* (2013.01); *A61K 51/088* (2013.01); *C07K 14/7051* (2013.01); *C07K 14/70521* (2013.01); *C07K 14/70553* (2013.01); *C12N 5/0636* (2013.01); *A61K 2039/515* (2013.01); *A61K 2039/54* (2013.01); *C07K 2319/03* (2013.01); *C07K 2319/74* (2013.01); *C12N 2510/00* (2013.01)

(58) Field of Classification Search
CPC .................................................. C07K 14/723
See application file for complete search history.

(56) References Cited

U.S. PATENT DOCUMENTS

| 5,686,281 A | 11/1997 | Roberts |
|---|---|---|
| 5,712,149 A | 1/1998 | Roberts |
| 6,083,751 A | 7/2000 | Feldhaus et al. |
| 7,052,906 B1 | 5/2006 | Lawson et al. |
| 7,176,187 B2 | 2/2007 | Kundra |
| 8,021,668 B2 | 9/2011 | Jin et al. |
| 2008/0311130 A1* | 12/2008 | Jin .................... C07K 14/70546 424/173.1 |
| 2013/0287681 A1 | 10/2013 | Kundra |
| 2014/0242701 A1* | 8/2014 | Shiku ................. C07K 14/7051 435/455 |
| 2015/0139943 A1 | 5/2015 | Campana et al. |

OTHER PUBLICATIONS

Ogawa et al. ("Expression of intercellular adhesion molecule-I in invasive breast cancer reflects low growth potential, negative lymph node involvement, and good prognosis." Clin Cancer Res 1998;4:31-36). (Year: 1998).*
International Search Report dated Nov. 24, 2017 in International Application No. PCT/US17/46630.
Jin, "Directed evolution to probe protein allostery and integrin I domains of 200,000-fold higher affinity", PNAS, vol. 103, No. 15, Apr. 11, 2006, pp. 5758-5763.
Liu, et al., "Affinity-Tuned ErbB2 or EGFR Chimeric Antigen Receptor T Cells Exhibit an Increased Therapeutic Index against Tumors in Mice", Cancer Research, vol. 75, Issue 17, Sep. 1, 2015, pp. 3596-3607.
Sadelain, et al., "The Basic Principles of Chimeric Antigen Receptor Design", Cancer Discov. vol. 3, Issue 4, Apr. 2013, pp. 388-398.
Vedvyas, et al., "A new genetic reporter for PET imaging of adoptively transferred T cells and their localization in tumors", J Nucl Med, vol. 57 No. supplement 2 116, May 1, 2016, 2 pages.
Weitz-Schmidt, et al., "Improved Lymphocyte Function-associated Antigen-1 (LFA-1) Inhibition by Statin Derivatives", The Journal of Biological Chemistry, vol. 279 (45), Nov. 2004, pp. 46764-46771.

* cited by examiner

*Primary Examiner* — Scott Long
(74) *Attorney, Agent, or Firm* — Perkins Coie LLP; Viola T. Kung

(57) ABSTRACT

The present invention relates to chimeric antigen receptors (CARs) specific to ICAM-1 comprising I domain of the $\alpha_L$ subunit of human lymphocyte function-associated antigen 1 (LFA-1). The invention particularly relates to CARs comprising human I domains having different affinities (1 mM to 1 nM Kd) to ICAM-1. CAR T cells comprising human I domain having a low affinity (1 to 200 µM Kd) to ICAM-1 can avoid targeting healthy tissues with basal ICAM-1 expression while simultaneously exhibiting increased potency and long-term efficacy against tumor tissues with high ICAM-1 expression. The present invention also relates to an adoptive cell therapy method for treating cancer by administering the CAR-T cells comprising human I domain to a subject suffering from cancer, whereby the CAR T cells bind to the cancer cells overexpressing ICAM-1 and kill the cancer cells.

13 Claims, 13 Drawing Sheets
Specification includes a Sequence Listing.

Top Panel

Bottom Panel

I DOMAIN CHIMERIC ANTIGEN RECEPTOR SPECIFIC TO ICAM-1

This application claims the benefit of U.S. Provisional Application Nos. 62/383,139, filed Sep. 2, 2016; and 62/419,817, filed Nov. 9, 2016; which are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Jul. 17, 2017, and a size of 9.89 kilobytes. The Sequence Listing filed via EFS-Web is part of the specification and is hereby incorporated in its entirety by reference herein.

FIELD OF THE INVENTION

The present invention relates to chimeric antigen receptors specific to ICAM-1 comprising human I domain. The invention particularly relates to chimeric antigen receptors comprising human I domains having different affinities (1 mM to 1 nM) to ICAM-1.

BACKGROUND OF THE INVENTION

Immunotherapy is emerging as a highly promising approach for the treatment of cancer. Genetically modifying T cells with CARs is a common approach to design tumor-specific T cells. CAR (chimeric antigen receptor)-T cells targeting tumor-associated antigens can be infused into patients (adoptive cell transfer or ACT) representing an efficient immunotherapy approach. The advantage of CAR-T technology compared with chemotherapy or antibody is that reprogrammed engineered T cells can proliferate and persist in the patient and work like a living drug.

CAR molecules are composed of synthetic binding moieties, typically an antibody-derived single chain fragment variable (svFv) or any native antigen-sensing element, fused to intracellular signaling domains composed of the TCR zeta chain and costimulatory molecules such as CD28 and/or 4-1BB[1,2]. The advantages of CAR mediated targeting include: 1) the provision of activation, proliferation, and survival signals in-cis via a single binding event, compared to the natural, non-integrated TCR and costimulatory signaling; 2) the ability to bypass the downregulation of MHC by tumor cells through MHC-independent antigen recognition; and 3) a reduced activation threshold as well as recognition of tumor cells with low antigen density enabled by the high affinity interaction between CAR and antigen[3,4].

The ideal CAR target antigen would be a native, surface-exposed tumor neoantigen that is highly expressed and is undetectable in healthy tissues. However, due to the implicit rarity of such antigens, many commonly targeted solid tumor antigens, are also expressed by non-tumor tissues, albeit at lower levels. CAR molecules with high affinity to such antigens can lead to collateral targeting of healthy tissues resulting in on-target, off-tumor toxicity, a major limiting factor to the progress of CAR T cell therapy to date.

Conventional CARs are constructed using a single-chain antibody format, and are selectively engineered to possess sub- to low nanomolar affinities for target antigens. However, increased CAR T cell sensitivity may be an advantage only when targeting true tumor antigens or those with the highest levels of restriction[17,36]. Otherwise, increased sensitivity comes at the price of reduced selectivity with lysis of target-expressing cells in a manner largely insensitive to antigen density[18].

There exists a needs for CARs with improved therapeutic index, i.e., CARs that can kill tumor while minimizing systemic toxicity.

BRIEF DESCRIPTION OF THE DRAWINGS

FIG. 1A: Schematic of LFA-1 in complex with ICAM-1. $\alpha$ and $\beta$ chains, and modular domains of LFA-1 integrin are labeled. Metal ions necessary for LFA-1 and ICAM-1 interaction are shown in circles.

FIG. 1B: Structural model of LFA-1 I domain and the N-terminal domain of ICAM-1 (D1) are drawn in ribbon diagram. N and C-termini, and mutational hot spots are indicated.

FIG. 1C: SPR sensogram of I domain variants binding to immobilized human ICAM-1, except F265S/F292G*, which was flowed over murine ICAM-1 (adapted from FIG. 2 of Jin et. al.[54], and FIG. 1 of Wong et. al[55]).

FIG. 1D: A schematic of the lentivirus vector encoding I domain CAR. LTR=long terminal repeat; SD=splice donor; SA=splice acceptor; $\psi^+$=packaging signal; SS=signal sequence; TM=transmembrane; Cyt=cytosolic domain.

FIG. 1E: Anti-Myc antibody binding to Jurkat T cells transduced with Myc-tagged CARs (TM, F292G, F292A, and WT I domain). NT=non-transduced.

FIG. 1F: Recombinant ICAM-1-Fc binding to CARs expressed in HEK 293T cells.

FIG. 1G: V-bottom adhesion assay measuring relative binding affinities between I domain CARs expressed in Jurkat T cells and soluble human (top) and murine (bottom) ICAM-1 (CD54) coated surfaces. n=3; p<0.01 for * vs. NT by Dunnett's multiple comparisons test.

FIG. 2A: Effector to target (E:T) assay for measuring target killing by primary T cells transduced with different I domain CARs. Each target was separately incubated with TM, F292G, F292A or WT CAR T cells at 5:1 E:T ratio. Percent viability was normalized to luminescence from target cells incubated with NT T cells (n=3, ±=standard deviation (SD)). A variable slope sigmoidal curve equation was used to fit data. p<0.01 for * vs. NT by Dunnett's multiple comparisons test.

FIG. 2B: The best fit values of 50% killing and Hill slope of the sigmoidal equation were plotted against the affinities of I domain CARs. The best fit values with r-square values higher than 0.85 were plotted.

FIG. 2C: ICAM-1 expression in primary T cells in comparison to HeLa cells. Grey and black histograms correspond to unlabeled cells and R6.5 antibody-labeled cells, respectively.

FIG. 2D: IFN-γ release was measured by ELISA for each CAR T variant after co-incubation with different target cells for 24 h (n=3). p<0.01 for * vs. 8505C/-ICAM-1 by Dunnett's multiple comparisons test.

FIG. 3A: Whole-body luminescence imaging was used to estimate tumor burden in mice infused with different CAR T cell variants 8 days post-tumor implantation. No T=mice received no T cells.

FIG. 3B: Mice were treated with CAR T cells 10 days post tumor implantation. NT=non-transduced T cells.

FIG. 3C: Survival curves of mice receiving different treatments. Log-rank (Mantel-Cox) test P values versus NT are not-significant for No T and TM, and p=0.008 for F292G, p=0.025 for R6.5, and p=0.0016 for F292A.

FIG. 4A: Schematic of SSTR2-I domain vector.

FIG. 4B: Longitudinal measurements of NOTAOCT uptake by PET/CT (top half of each panel), and tumor burden by whole body luminescence imaging (bottom half of each panel). Images are representative of four mice in each cohort. Whole body PET/CT images, taken on the day of maximum tracer uptake, are shown on the far right. Imaging time points are indicated below the bottom panel. For example, 15 represents 15 days post tumor xenograft (and 7 days post T cell infusion).

FIG. 4C: Quantification of luminescence and tracer uptake in the lungs of mice treated as indicated. Top Panel: NT (non-transduced) T cells. Bottom level: CARs-F292A.

FIG. 4D: Cytokine levels measured from blood drawn at various time points from the same mice in 'b' and 'c' are plotted (mean±SD, duplicate measurements). Top Panel: NT (non-transduced) T cells. Bottom level: CARs-F292A.

DETAILED DESCRIPTION OF THE INVENTION

Definitions

Figure 1A:
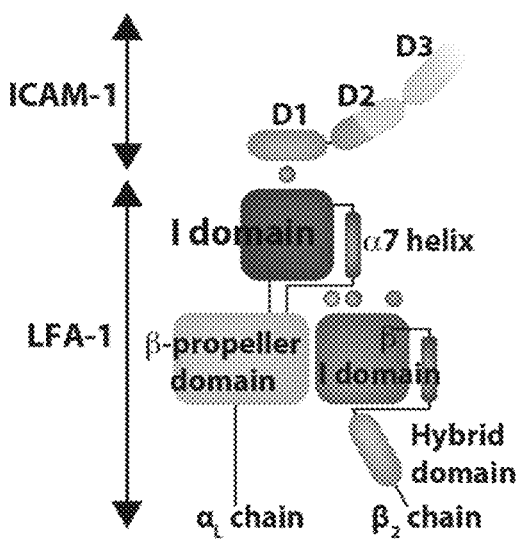
FIGS. 1A-1G show construction of ICAM-1 specific CARs with step-wise, $10^6$-fold variations in affinity and their in vitro results.

As used herein, "about" refers to ±10% of the recited value.

As used herein, "adoptive T cell therapy" involves the isolation and ex vivo expansion of tumor specific T cells to achieve greater number of T cells than what could be obtained by vaccination alone. The tumor specific T cells are then infused into patients with cancer in an attempt to give their immune system the ability to overwhelm remaining tumor via T cells which can attack and kill cancer.

As used herein, "affinity" is the strength of binding of a single molecule (e.g., I domain) to its ligand (e.g., ICAM-1). Affinity is typically measured and reported by the equilibrium dissociation constant ($K_D$ or Kd), which is used to evaluate and rank order strengths of bimolecular interactions.

As used herein, a "chimeric antigen receptor (CAR)" means a fused protein comprising an extracellular domain capable of binding to an antigen, a transmembrane domain derived from a polypeptide different from a polypeptide from which the extracellular domain is derived, and at least one intracellular domain. The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a particular structure independently of other regions.

As used herein, "integrin" or "integrin receptor" (used interchangeably) refers to any of the many cell surface receptor proteins, also referred to as adhesion receptors which bind to extracellular matrix ligands or other cell adhesion protein ligands thereby mediating cell-cell and cell-matrix adhesion processes. Binding affinity of the integrins to their ligands is regulated by conformational changes in the integrin. Integrins are involved in physiological processes such as, for example, embryogenesis, hemostasis, wound healing, immune response and formation/maintenance of tissue architecture. Integrin subfamilies contain a beta-subunit combined with different alpha-subunits to form adhesion protein receptors with different specificities.

"Intercellular adhesion molecule-1" or "ICAM-1", i.e. GenBank Accession Nos. NM_000201, NP_000192, is the ligand for $\alpha_L\beta_2$ integrin, and its N-terminal domain (D1) binds to the $\alpha_L$ I domain through the coordination of ICAM-1 residue Glu-34 to the MIDAS metal. ICAM1 is typically expressed on endothelial cells and cells of the immune system. ICAM1 binds to integrins of type $\alpha_L\beta_2$ and $\alpha_M\beta_2$. ICAM-1 is upregulated in several carcinomas and the associated stroma[24] as well as in inflammatory conditions[25]. Aside from diseased tissues, ICAM-1 is basally expressed in several cell types including endothelial cells, immune cells, and some epithelial cells[25].

"Lymphocyte function-associated antigen-1", "LFA-1", "$\alpha_L\beta_2$ integrin" or "CD18/CD11a" refers to a member of the leukocyte integrin subfamily. LFA-1 is found on all T-cells and also on B-cells, macrophages, neutrophils and NK cells and is involved in recruitment to the site of infection. It binds to ICAM-1 on antigen-presenting cells and functions as an adhesion molecule.

As used herein, "I domain" refers to the inserted or I domain of the $\alpha_L$ subunit of LFA-1, and is an allosteric mediator of ligand binding to LFA-1. I domain is a native ligand of ICAM-1. The ligand binding site of the I domain, known as a metal ion-dependent adhesion site (MIDAS), exists as two distinct conformations allosterically regulated by the C-terminal α7 helix. A wild-type (WT) I domain encompasses amino acid residues 130-310 of the 1145 amino acid long mature $\alpha_L$ integrin subunit protein (SEQ ID NO: 1, which is the amino acid residues 26-1170 of GenBank Accession No. NP_002200). All numbering of amino acid residues as used herein refers to the amino acid sequence of the mature $\alpha_L$ integrin (SEQ ID NO: 1), wherein residue 1 of SEQ ID NO: 1 corresponds to residue 26 of the sequence of GenBank Accession No. NP_002200.

As used herein, a "tumor antigen" means a biological molecule having antigenicity, expression of which causes cancer.

Description

The present invention provides chimeric antigen receptors targeting ICAM-1, which is a broad tumor biomarker, using its physiological ligand, LFA-1. The inventor has constructed a panel of affinity-variant CARs that comprise human I domain; the CARs having 1 mM to 1 nM affinity to ICAM-1. The present invention provides ICAM-1-specific CARS with broad anti-tumor applicability. CAR T cells comprising I domain having micromolar affinity targeting ICAM-1 have improved efficacy and safety over conventional CARS, as they are capable of lysing cells overexpressing target antigens while sparing normal cells with much lower densities.

The present invention is directed to a chimeric antigen receptor fusion protein comprising from N-terminus to C-terminus: (i) a human I domain of the $\alpha_L$ subunit of lymphocyte function-associated antigen-1, (ii) a transmembrane domain, (iii) at least one co-stimulatory domains, and (iv) an activating domain.

Figure 1B:
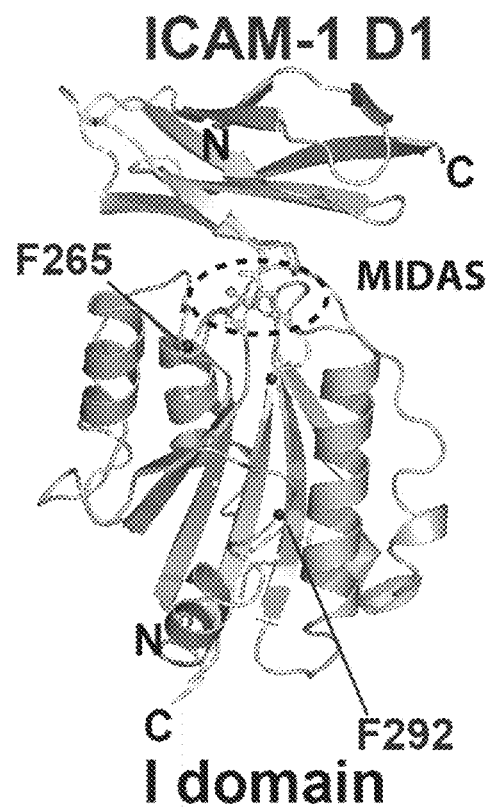

The CAR of the present invention comprises (i) a human I domain that binds specifically to ICAM-1. I domain specific to ICAM-1 can be built using the I domain derived from LFA-1 (FIGS. 1A and 1B). Various activating point mutations in the I domain are localized outside of the binding interface that includes a region known as the metal-ion dependent adhesion site (MIDAS) (FIG. 1B). Mutants containing the step-wise elevation of I domain affinity to ICAM-1 from 1 mM to 1 nM can be obtained by screening a library of mutants for their higher binding to ICAM-1 coated surface, beads, or cells. For example, different affinity mutants can be isolated using a yeast display system (see Jin et al.[27]). Affinity is first measured by surface plasmon resonance (e.g., Biacore) to assess 1:1 binding affinity between I domain and ICAM-1. Affinity of ICAM-1 to CAR expressed on cells can be measured by flow cytometry and using the Langmuir isotherm equation. Likewise, Scatchard analysis can be performed to estimate CAR affinity by measuring the amounts of free and cell-surface bound ligand (in this case, radio- or fluorescence-labeled ICAM-1).

Figure 1C:
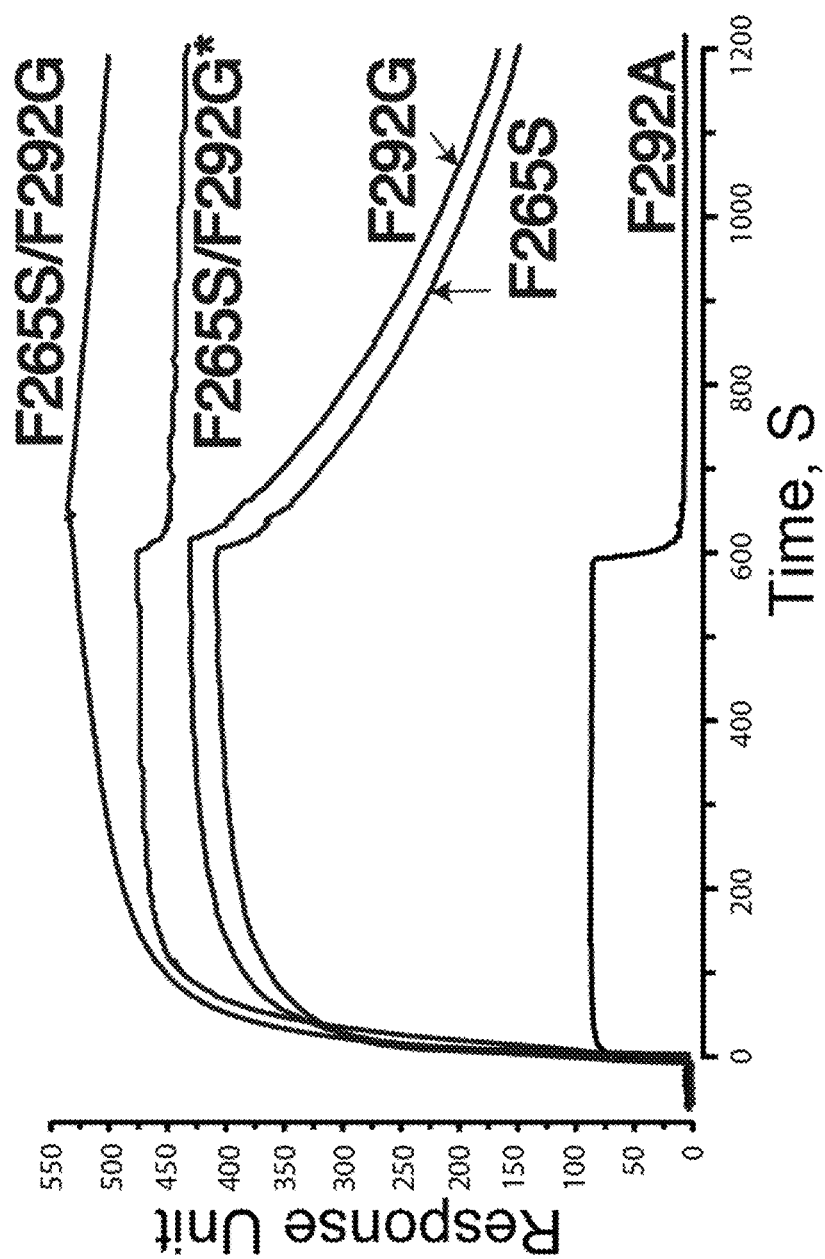

Table 1 shows measured affinities of LFA-1 I domains of wild type and mutants to ICAM-1. A majority of mutations are changing hydrophobic bulky side chains (F, L, I) into more hydrophilic (A, S, T), thereby disrupting the structure of more compact, low affinity I domain conformation. For example, substitution of Phe-292 located in the C-terminal α7-helix with Ala (F292A) and Gly (F292G) provides to affinities ($K_D$) of ~20 µM and 0.1 respectively (Table 1). The combination of F292G with another comparably activating mutation in Phe-265 (F265S/F292G) provides an affinity of 6 nM, approximately 200,000-fold higher than the wild-type (WT) I domain ($K_D$=1.5 mM) (FIG. 1C). To lock the C-terminal α7-helix of F265S/F292G in the open position (FIG. 1A), Gly-311 can be replaced with Cys (G311C) in the F265S/F292G mutant (F265S/F292G/G311C, dubbed triple mutant or TM) to form a disulfide bond with the naturally unpaired Cys-125 (Table 1). Therefore, the monovalent affinities of individual I domain variants for ICAM-1 can be designed to span approximately six orders of magnitude ($K_D$~1 nM to 1 mM), as measured by surface plasmon resonance (SPR) or estimated by flow cytometry (FIG. 1C, Table 1). The mutants in Table 1 are for illustration purpose only; the CARs of the present invention are not limited to these specific mutants. Mutants that have other mutations and have affinities to ICAM-1 between 1 mM to 1 nM can be made, tested, and selected according to methods known to a skilled person.

TABLE 1

| Name | Sequence of SEQ ID NO: 1 | Affinity |
|---|---|---|
| Wild-type (WT) | G128-G311 | 1.5 mM* |
| I288N | G128-G311 | 202 µM** |
| I309T | G128-G311 | 127 µM** |
| L295A | G128-G311 | 37 µM** |
| F292A | G128-G311 | 20 µM* |
| F292S | G128-G311 | 1.24 µM** |
| L289G | G128-G311 | 196 nM** |
| F292G | G128-G311 | 119 nM* |
| F265S | G128-G311 | 145 nM* |
| F265S/F292G (DM) | G128-G311 | 6 nM* |
| F265S/F292G/G311C (TM) | E124-S313 | ~1 nM* |
| R6.5 | scFv | 10 nM*** |

*SPR measurements;
**Estimated from flow cytometry mean fluorescence intensity (MFI) values of ICAM-1-Fc binding to yeast cells expressing I domain variants[5]. The equation used was Kd (M) = 0.00175*exp(−0.1542*MFI);
***Estimated from titrated R6.5 antibody binding to HeLa cells[34].

In one embodiment, the CAR of the present invention comprises I domain that is a wild-type human I domain, a mutant of wild-type human I domain having 1 to 3 amino acid mutations, or a sequence having at least 95%, or at least 96% identity, or at least 97% identity, or at least 98% identity, or at least 99% identity to the sequence of the wild-type I domain or the mutant, having an affinity of binding human ICAM-1 of 1 mM or stronger. In one embodiment, the mutant may have one or more mutations at the amino acid residue 265, 288, 289, 292, 295, 309, or 311 of the wild-type I domain. For example, the mutant may have one or more mutations of I288N, I309T, L295A, F292A, F292S, L289G, F292G, F265S, F265S/F292G, or F265S/F292G/G311C, of the wild-type I domain. In one embodiment, combining two I domain mutations produces a mutant with a higher affinity than that of each parent mutant. For example, combining two mutants each having about 100 µM Kd typically produces a mutant having about 1 to about 10 µM Kd range. F292G is a very potent point mutation; combining F292G with other mutations increases I domain affinity to ICAM-1 to stronger than 100 nM Kd. The above numbering of the amino acid residues is in reference to the mature amino acid sequence of SEQ ID NO: 1, and residue number 1 corresponds to the amino acid residue 26 of GenBank Accession No. NP_002200.

In one embodiment, the CAR of the present invention comprises I domain that binds ICAM-1 at an affinity between 1 mM to 1 nM Kd, preferably 1-200 µM Kd or 1-20 µM Kd.

In one embodiment, the CAR of the present invention comprises I domain that binds to ICAM-1 at an affinity between about 120 nM to about 1 nM Kd, e.g., F292G, F265S, F265S/F292G, and F265S/F292G/G311C.

In one embodiment, the CAR of the present invention comprises I domain that binds to ICAM-1 at an affinity between about 20 µM to about 120 nM Kd, e.g., F292A, F292S, and I289G.

In one embodiment, the CAR of the present invention comprises I domain that binds to ICAM-1 at an affinity between about 200 µM to about 20 µM Kd, e.g., I288N, I309T, L295A, and F292A.

In one embodiment, the CAR of the present invention comprises I domain that binds to ICAM-1 at an affinity between about 1 µM to about 100 µM Kd, e.g., L296A, F292A and F292S.

In one embodiment, the CAR of the present invention comprises I domain that binds to ICAM-1 at an affinity between about 1 mM to about 200 µM Kd, e.g., wild-type and I288N.

In one embodiment, the CAR of the present invention comprises I domain that binds to ICAM-1 at an affinity between about 1 mM to about 100 µM Kd, e.g., wild-type, I288N, and I309T. The affinities in the above embodiments refer to the interaction between I domain and ICAM-1 in solution.

One advantage of using human I domain in CAR construction is that human I domain binds murine ICAM-1 with comparable affinity to human ICAM-1 (2 nM vs. 6 nM respectively). Cross-reactivity with its murine homologue enables examination of on-target, off-tumor toxicity of I domain CAR T cells concurrently with on-target, on-tumor efficacy in preclinical mouse models with human tumor xenografts. This is an advantage of human I domain in predicting clinical toxicity in a preclinical model. In comparison, the R6.5 scFv (derived from the mouse hybridoma clone, R6.533) has a Kd of 10 nM for human ICAM-1 (Table 1) but does not cross-react with murine ICAM-1.

The CAR of the present invention comprises (ii) a transmembrane domain which spans the membrane. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3 zeta chain, CD28, CD3-epsilon, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. In preferred embodiments, the transmembrane domain is derived from CD28 or CD8, which give good receptor stability.

The CAR of the present invention comprises (iii) one or more co-stimulatory domains selected from the group consisting of human CD28, 4-1BB (CD137), ICOS-1, CD27, OX 40 (CD137), DAP10, and GITR (AITR). In embodiment, the CAR comprises two co-stimulating domains of CD28 and 4-1BB.

The endodomain (the activating domain) is the signal-transmission portion of the CAR. After antigen recognition, receptors cluster and a signal is transmitted to the cell. The most commonly used endodomain component is that of CD3-zeta (CD3 Z or CD3ζ), which contains 3 ITAMs. This transmits an activation signal to the T cell after antigen is bound. CD3-zeta may not provide a fully competent activation signal and additional co-stimulatory signaling may be needed. For example, one or more co-stimulating domains can be used with CD3-Zeta to transmit a proliferative/survival signal.

The CAR of the present invention may comprise a signal peptide N-terminal to the I domain so that when the CAR is expressed inside a cell, such as a T-cell, the nascent protein is directed to the endoplasmic reticulum and subsequently to the cell surface, where it is expressed. The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases. As an example, the signal peptide may derive from human CD8 or GM-CSF, or a variant thereof having 1 or 2 amino acid mutations provided that the signal peptide still functions to cause cell surface expression of the CAR.

The CAR of the present invention may comprise a spacer sequence as a hinge to connect I domain with the transmembrane domain and spatially separate antigen binding domain from the endodomain. A flexible spacer allows to the binding domain to orient in different directions to enable its binding to a tumor antigen. The spacer sequence may, for example, comprise an IgG1 Fc region, an IgG1 hinge or a CD8 stalk, or a combination thereof. A human CD28 or CD8 stalk is preferred.

The present invention provides a nucleic acid encoding the CAR described above. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBenk for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a Sendai virus vector, an Epstein-Barr virus (EBV) vector, and a HSV vector can be used. As the virus vector, a virus vector lacking the replicating ability so as not to self-replicate in an infected cell is preferably used.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+en-vAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

The present invention provides T cells or natural killer cells (NK cells) modified to express the CAR as described above. CAR-T cells or CAR-NK cells of the present invention bind to ICAM-1 via the I domain of CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, killing target cells, or the like as an index.

T cells or NK cells modified to express the I domain-CAR can be used as a therapeutic agent for a disease. The therapeutic agent comprises the T cells expressing the I domain-CAR as an active ingredient, and may further comprise a suitable excipient. Examples of the excipient include pharmaceutically acceptable excipients known to a person skilled in the art.

The present invention further provides an adoptive cell therapy method for treating cancer. The method comprises the steps of: administering the CAR-T cells or CAR-NK cells of the present invention to a subject suffering from cancer, wherein the cancer cells of the subject overexpress ICAM-1, and the CAR-T cells or CAR-NK cells bind to cancer cells to kill the cancer cells. "Overexpress", as used herein, refers to cancer cells have surface expression of ICAM-1 at least $10^5$ molecules per cell. In one embodiment, the CAR comprises I domain having an affinity to ICAM-1 between about 1 to about 1000 µM, preferably between about 1 to about 200 µM, or about 1 to about 20 µM. Cancers suitable to be treated by the present invention include, but not limited to thyroid cancer, gastric cancer, pancreatic cancer, and breast cancer.

By functionally investigating CAR affinities spanning step-wise across a $10^6$-fold range, concurrently with target cells with varying levels of antigen expression, the inventor systematically examined the influence of CAR affinity and antigen density on T cell efficacy in vitro and in vivo. T cell activation status in vitro, as measured by CD25, cytokine release, and cytotoxicity, was dependent on affinity and target antigen density, resulting in more potent T cell activation and target killing with increases in CAR affinity and antigen density. The activation threshold of nanomolar affinity CAR T cells (TM, F292G) was less dependent on antigen density compared to the micromolar affinity CAR T cells (F292A), reacting to antigen density as low as $10^4$ molecules/cell. In contrast, F292A CAR T cells rapidly lost the ability to lyse cells expressing target antigens below $10^5$ molecules/cell. Millimolar affinity CAR T cells (wide-type, WT) were largely unreactive to target cells with low to moderate levels of antigen, requiring a threshold antigen density of $10^6$ molecules/cell for detectable activation, cytokine release, and target lysis to occur.

Table 2 shows a range of desired affinities of I domain-comprising CART cells to ICAM-1, for targeting cells with specified ICAM-1 antigen density.

TABLE 2

| I CAM-1 Density (molecules/cells) | Suitable I Domain Affinity |
|---|---|
| $<10^4$ | about 120 nM-1 nM (e.g., TM, F292G) |
| $10^4$-$10^5$ | about 20 µM-120 nM (e.g., F292S, F265S) |
| $10^5$-$10^6$ | about 200 µM-20 µM (e.g., F292A) |
| $\geq 10^6$ | about 1.5 mM-200 µM (e.g., WT) |

The quantitative harmony between CAR affinity and anti-tumor potency in vitro is discordant with quantitative in vivo observations whereby micromolar affinity (1-200 µM or 1-20 µM) CAR-T cells or CAR-NK cells are superior to higher affinity CAR-T cells or CAR-NK cells as measured by the rate of expansion at the tumor site, the rate of tumor eradication, frequency of tumor relapse, and levels of on-target, off-tumor toxicity.

The ability of I domain CAR-T cells or CAR-NK cells to cross-react with murine ICAM-1 allows for a rigorous and simultaneous assessment of the efficacy of CAR-T cells or CAR-NK against human tumor cells and on-target, off-tumor toxicity against murine ICAM-1 on healthy tissues. By simultaneous expression of a reporting gene, human somatostatin receptor 2 (SSTR2), and I domain CAR on T cells followed by longitudinal position emission tomography (PET) imaging, in vivo spatiotemporal mapping of adoptively transferred T cells can be achieved.

Onset of toxicity appears to be dependent on CAR affinity and tumor-burden, as demonstrated by the uniform fatalities in mice treated with the highest affinity (TM) CAR T cells, the increased rate of toxicity observed in F292G CAR-treated mice with larger tumor burden, and the absence of detectable toxicity after treatment with micromolar affinity F292A CAR T cells.

CARs comprising high affinity mutants (about 120 nM-1 nM) have high potency and they are capable to bind T cells with low ICAM density of less than $10^4$ per cell.

CARs possessing affinities in the micromolar range (e.g. about 1-200 µM Kd) minimize off-tumor toxicity against basally expressed antigens in normal tissues, and also increases therapeutic index, in comparison with CARs having affinities in the nanomolar range (e.g., about 1-200 nM Kd). CAR T cells with target affinities in the micromolar range can avoid targeting healthy tissue with basal antigen expression while simultaneously exhibiting increased potency and long-term efficacy against tumor tissue with high target expression. The micromolar affinity CAR (such as F292A-I domain) enables T cells to neglect tissues expressing less than $10^5$ molecules/cell, a threshold which anaplastic thyroid tumors surpass yet healthy tissues typically do not. Engagement of target antigen by nanomolar affinity CAR T cells (e.g., TM, F292G, and R6.5 CAR) may result in an unnaturally slow off rate, deviating from transient and dynamic nature of interactions natively found between TCRs and pMHCs[48]. High affinity and avidity interactions by CAR can reduce T cells' propensity for serial killing, potentially causing exhaustion or increased susceptibility to activation-induced cell death[49]. Although CAR T cells with nanomolar affinity to ICAM-1 may work, they may be operating sub-optimally and may be more prone to exhaustion and excessive cytokine release, ultimately facilitating off-tumor toxicity or tumor relapse.

The following examples further illustrate the present invention. These examples are intended merely to be illustrative of the present invention and are not to be construed as being limiting.

EXAMPLES

Materials and Methods

Example 1. Cell Lines and Primary Human Lymphocytes

Human dermal microvascular endothelial cells (HMEC-1) were obtained from the Center for Disease Control and were cultured in MCDB 131 medium (Invitrogen) supplemented with 10% (v/v) fetal bovine serum (FBS, Atlanta Biologicals), 10 mM L-alanyl-L-glutamine dipeptide (Gibco), 100 units/ml Penicillin-Streptomycin (Pen-strep), 1 µg/ml hydrocortisome (MP Biomedicals), and 10 ng/ml recombinant human epidermal growth factors (Invitrogen). Mouse brain microvascular endothelial cells (bEnd.3, ATCC) were maintained in Advanced Dulbecco's Modified Eagle Medium (ADMEM, Invitrogen) supplemented with 4 mM L-glutamine, 100 units/ml Pen-strep, and 10% FBS. HeLa cells (ATCC) were cultured in ADMEM containing 10% FBS, 2 mM L-glutamine, and 100 units/ml Pen-strep. 8505C cells (DSMZ) were cultured in RPMI-1640 medium (Invitrogen) containing 10% FBS, 2 mM L-glutamine, and 100 units/ml Pen-strep. HMEC-1, bEnd.3, HeLa, and 8505c cells were transduced with lentivirus encoding Firefly Luciferase-F2A-GFP (Biosettia) and sorted based on fluorescence.

Human peripheral blood was obtained from healthy volunteer donors by venipuncture. Peripheral blood mononuclear cells were isolated using Ficoll-Paque PLUS (GE Healthcare) and cultured in Optimizer CTS T-cell Expansion SFM (Thermo) supplemented with 5% human AB serum (Sigma), 2 mM L-alanyl-L-glutamine dipeptide, and 30 IU/ml human IL-2 (Cell Sciences) (T cell culture medium). Non-adherent cells were removed after 24 h and enriched for T cells with Dynabeads CD3/CD28 T cell expander (Thermo) at a 2:1 bead to T cell ratio. Dynabead-bound T cells were subsequently cultured in IL-2 containing media at a density of $1 \times 10^6$ cells/ml. All cells were incubated at 37° C. in a 5% $CO_2$ humidified incubator.

Example 2. Construction of I Domain CAR Vector

Genetic sequences encoding LFA-1 I domains of varying affinities to ICAM-1 were derived from a previous study[27].

I domain variants were fused at the C-terminus directly to the CD8 hinge, CD28 transmembrane domain, and the intracellular portions of the 3$^{rd}$ generation CAR architecture incorporating the cytoplasmic domains of CD28, CD137, and CD3ζ. The complete CAR inserts were then subcloned into a pLenti backbone[29]. A reporter gene for CAR T cell imaging, SSTR2, was linked to I domain at the N-terminus using a 'ribosome skipping' porcine teschovirus-1 2A (P2A) sequence to ensure comparable production of CAR and SSTR2 from the same mRNA.

Example 3. Lentivirus Production and Transduction of T Cells

Lentivirus was produced by transiently transfecting HEK 293T cells using calcium phosphate. Briefly, 10 μg of transfer gene, 7.5 μg of pCMV-dR8.2 (Addgene) and 5 μg of pCMV-VSVG (Addgene) were mixed and incubated with 2 M CaCl$_2$ followed by 2×HBSS. Resulting solutions were added dropwise to 10 cm$^2$ cell culture dishes seeded with 3.2×10$^6$ HEK 293T cells in 10 ml DMEM 24 h previously. Transfection media was replaced after 6 h. Media containing lentivirus was harvested at 48 and 72 h post transfection, filtered through 0.45 μm filters, and concentrated by ultracentrifugation at 75,000×g for 2 h at 4° C. Lentivirus was then resuspended in serum containing media and frozen at −80° C. Human T cells were transduced 24-72 h post activation with anti-CD3/CD28 Dynabeads either by spinfection (1,000 g for 1 h at 32° C.) or by overnight incubation with lentivirus. T cells were transduced once more 24 h after the first transduction. During and following transductions, media containing IL-2 was replaced with media containing human IL-7 (10 ng/ml) and IL-15 (5 ng/ml) (Peprotech). Jurkat T cells were transduced by a single overnight incubation with lentivirus.

Example 4. In vitro Target Cell Killing Assay

2×10$^5$ target cells (HMEC-1, bEnd.3, HeLa, and 8505c) stably transduced to express GFP and firefly luciferase were co-cultured with either non-transduced or I domain CAR T cells at varying effector to target ratios (E:T). In certain conditions, the ICAM-1 gene was disrupted in 8505C cells using CRISPR/Cas9 (Santa Cruz, #sc-400098; denoted as 8505C/-ICAM-1) or, alternatively, 8505C cells were exposed to 1 μg/ml lipopolysaccharide (LPS; *Escherichia coli* O26:B6, Sigma) for 12 h to induce overexpression of ICAM-1 (denoted as 8505C/LPS). Co-cultures were carried out in T cell culture medium containing 150 μg/ml D-Luciferin (Gold Biotechnology) and no cytokine supplementation. Luminescence was measured using a plate reader (TECAN infinite M1000 PRO) with readings in each E:T condition normalized to the non-transduced T cell:target co-culture controls.

Example 5. 8505C Mouse Model, Whole-body Tumor Imaging, and Serum Cytokine Analysis 7.5×10$^5$ 8505C cells were injected into NSG mice via tail vein. 1-3×10$^6$ T cells were injected via tail vein 8-10 days after tumor cell injection. Injection timing was chosen based on prior studies with R6.5 CAR T cells which demonstrated tumor elimination using similar CAR dosages at up to 10-days post xenograft[29]. Luminescence imaging of tumor xenografts in live mice was performed using a whole body optical imager (In-Vivo Extreme, Bruker). Mice were anesthetized with 2% isoflurane in 2 L/min O$_2$. Tumor burden was quantified through integration of luminescence over chest cavity and the entire mouse body. For serum cytokine analysis, 50-100 μl of blood was collected via tail-vein into Eppendorf tubes on ice. Plasma was immediately isolated after removing cell pellet by centrifugation at 2,000 g for 10 min at 4° C., and stored at −80° C. Human cytokines (GM-CSF, IL-2, IL-6, IFN-γ, TNF-α, CXCL10) were measured in duplicate using Bio-Plex MAGPIX (Bio Rad) according to the manufacturer's instructions.

Example 6. Ex vivo Cellular Analysis

Tumor xenografts were resected from mice at appropriate time points. Resected tumors were diced and flushed through 80 μm cell strainers to yield single cell suspensions. Red blood cells were lysed by incubation with 1×RBC lysis buffer (eBiosciences). Remaining cells were washed, resuspended in 1×HBSS containing 2% normal goat serum, and blocked with mouse IgG at 2 μg/ml for 10 min. This was followed by staining with 1 μg/ml Propidium Iodide (Invitrogen) in combination with 2 μg/ml mouse anti-human CD3-Alexa Fluor 647 (Biolegend) or 2 μg/ml rabbit anti-c-myc-Alexa Fluor 647 (Biolegend). Resulting cells were acquired on a Gallios flow cytometer (Beckman Coulter). Initial flow cytometry gates were determined based on live cell gating (Propidium Iodide negative).

Example 7. ICAM-1 and CAR Expression Quantification

ICAM-1 expression on various cell lines was determined using a mouse anti-human R6.5 monoclonal antibody (10 μg/ml) obtained from hybridoma (ATCC). I domain CAR expression on T cells was detected using 2 μg/ml rabbit anti-c-myc-Alexa Fluor 647 (Biolegend). I domain Jurkat T cell variants were incubated with 10 μg/ml recombinant human ICAM-1 fused to human Fcγ (R&D Systems). Cells were then washed and resuspended in 1 μg/ml rabbit anti-human PE (Santa Cruz Biotechnology) prior to flow cytometry analysis.

Example 8. In vitro Measurement of IFN-γ

Target cells were washed and suspended at 1×10$^6$ cells/ml in T cell culture medium without cytokines. 100 μl of each target cell was added in triplicate to a 96-well round bottom plate (Corning). T cells resuspended at 5×10$^6$ cells/ml in T cell culture medium were combined with target cells in appropriate wells. Plates were incubated at 37° C. for 24-48 h. After incubation, supernatants were collected for ELISA to detect IFN-γ (Biolegend).

Example 9. CD25 and CD69 Staining

Jurkat cells modified with I domain CARs were co-cultured with target cells at an effector to target ratio of 1:1 (1×10$^5$ effectors: 1×10$^5$ targets) in a 96-well plate. The plate was incubated at 37° C. for 6 h. After incubation, cells were washed prior to labelling with 2 μg/ml anti-human CD25-allophycocyanin (APC; Biolegend) for 30 min on ice. After incubation, samples were washed and analyzed by flow cytometry. As an alternative to ICAM-1 expressing cells, we also used microbeads coated with known amounts of ICAM-1. 1×10$^6$ sulfate latex microbeads (8 □m, ThermoFisher Scientific) were resuspended in 100 uL of PBS containing indicated amounts of human or murine recombinant ICAM-1-Fcγ (R&D Systems) conjugated with Cy5.5 (Sulfo-Cyanine5.5 NHS ester, Lumiprobe) overnight at room temperature with gentle mixing. Protein-labeled particles were pelleted and resuspended in fresh PBS containing 0.1 M glycine pH 7.4 for 1 h, while supernatant was used to measure bead adsorption efficiency by fluorescence (TECAN infinite M1000 PRO). After saturation of bead surface with glycine, beads were pelleted and resuspended in PBS containing 5 mM $MgCl_2$. Jurkat cells modified with each I domain CAR variant were incubated with ICAM-1-bound latex beads at 1:3 (cell:bead) ratio overnight at 37° C. Cells were then collected, labeled with 2 μg/ml anti-human CD69-APC (Biolegend) for analysis by flow cytometry.

Example 10. V-bottom Adhesion Assay

V-bottom 96-well plates (Corning) were coated with either murine or human ICAM-1-Fcγ (10 μg/ml in PBS, pH 7.4) or 2% BSA at 4° C. overnight. The plates were then blocked with 2% BSA for 1 h at 37° C. I domain CAR T clones were first stained with CellTracker Orange according to manufacturer's protocol and then added to ICAM-1-coated wells in 50 μl of PBS containing 5 mM $MgCl_2$ and 1% BSA. Plates were immediately centrifuged at 200 g for 15 min at room temperature. Nonadherent cells that accumulated at the bottom of the V-bottom plates were quantified by a fluorescence plate reader (TECAN infinite M1000 PRO). Cell binding to ICAM-1 was calculated from the fluorescence intensity values of experimental measurements ($F_{CAR}$ and $F_{NT}$) and normalized to the fluorescence from the wells coated with BSA alone ($F_{BSA}$): $100\times((F_{BSA}-F_{CAR})/F_{BSA})/((F_{BSA}-F_{NT})/F_{BSA})$.

Example 11. Labeling of $^{18}$F-NOTA-octreotide (NOTAOCT)

NOTAOCT (1,4,7-Triazacyclononane-1,4,7-triacetic acid-octreotide[30], GMP grade) was obtained as a 1 mg lyophilized powder (cat #9762, ABX Pharmaceuticals). The NOTAOCT vial content was diluted with 18 MW water to 200 μl (5 mg/ml solution) and stored at 4° C. as a stock solution. For chelation of NOTA with Fluorine-18[31], 5 μl of NOTAOCT was added to 10 μl of 0.1 M sodium acetate, pH 4, 6 μl of 2 mM AlCl3, and 100 μl containing ~30 mCi [18]F. The solution was immediately placed in a Thermomixer (Eppendorf) at 100° C. and incubated for 15 minutes followed by cooling to room temperature and dilution in 15 ml $ddH_2O$. A Sep-Pak light C18 column was regenerated in 3 ml 100% ethanol and washed twice in 5 ml $ddH_2O$ with an observed flow rate of 10 drops per minute. NOTAOCT was then loaded to the Sep-Pak column, which was later washed in 15 ml 18 MW water to eliminate any remaining free [18]F. Trapped NOTAOCT was eluted from the column using 300 μl of ethanol and diluted to 1.5 ml with PBS for injection, providing the final product in ~15% ethanol isotonic, injectable solution. The eluent was passed through 0.2 μm filter. The purity of the final product was checked by reverse phase HPLC.

Example 12. PET/CT Imaging

Registered CT images were acquired using a micro-PET/CT scanner (Inveon, Siemens) at 1-2 h post NOTAOCT injection. Projection data was acquired in a cone-beam geometry with approximately 1 s steps at 1 degree angular increments. At least 10 million coincidence events were acquired for PET per study using a 250 to 750 keV energy window and a 6 ns timing window. A reference tube containing 100 μl of a 10% $ID/cm^3$ equivalent dose for quantification of NOTATOC uptake in vivo. To compute NOTAOCT uptake within mouse lungs, ellipsoids were drawn separately on the left and right sides of lungs to enclose the majority of their footprint. The % $ID/cm^3$ values, computed relative to the counts obtained in the reference tube, were approximated to a standard uptake value ($SUV^{32}$) by dividing % $ID/cm^3$ by four, assuming injection efficiency of 100% and 25 g of body weight. Visualization and analyses of PET/CT images were performed using AMIDE software (http://amide.sourceforge.net).

Example 12. Histology

After euthanasia, mouse lungs were perfused via trachea with 4% paraformaldehyde, and each of five lobes were separated post fixation and embedded in paraffin. Tissues were cut to produce 5 μm sections (Microtome, Leica). Paraffin embedded sections were stained with hematoxylin and eosin (H&E) or hematoxylin only for CD3 and GFP immunostaining (performed by HistoWiz, Inc.). Histological analysis was performed by an experienced pathologist.
Results
Statistical Analysis One-way ANOVA, Dunnett's multiple comparisons test, and unpaired Student's t-test were performed using Prism (GraphPad) on data indicated.

Example 13. ICAM-1 Specific CAR T Cells with $10^6$-Fold, Step-wise Variation in Affinity CAR constructs specific to ICAM-1 were built using the I domain derived from LFA-1 (FIGS. 1A-B; Table 1), according to Jin et al[27] and U.S. Pat. No. 8,021,668.

Figure 1D:
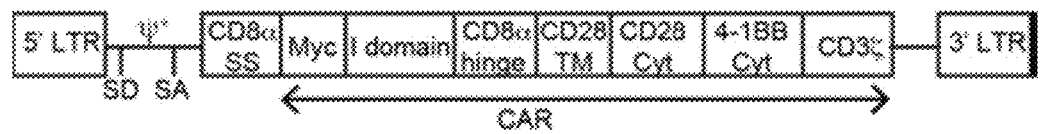
Figure 1E:
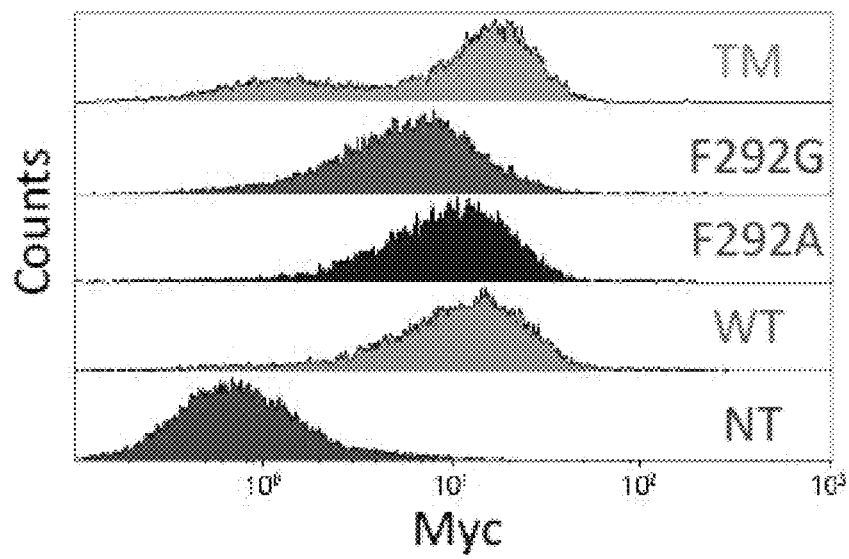
Figure 1F:
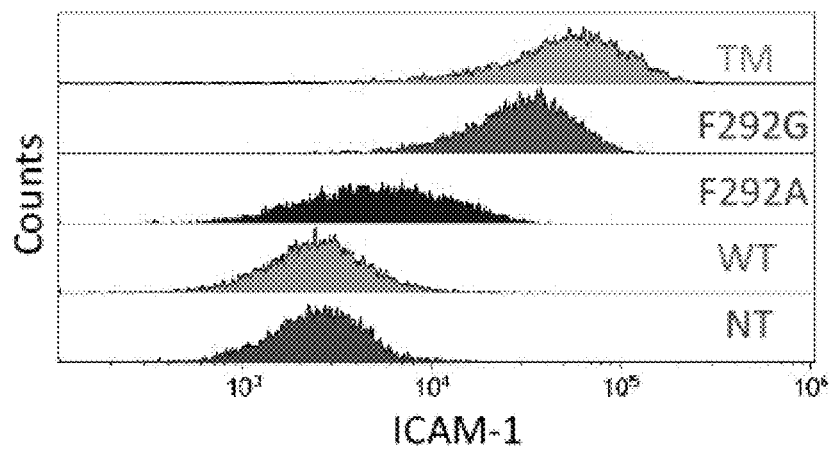
Figure 1G:
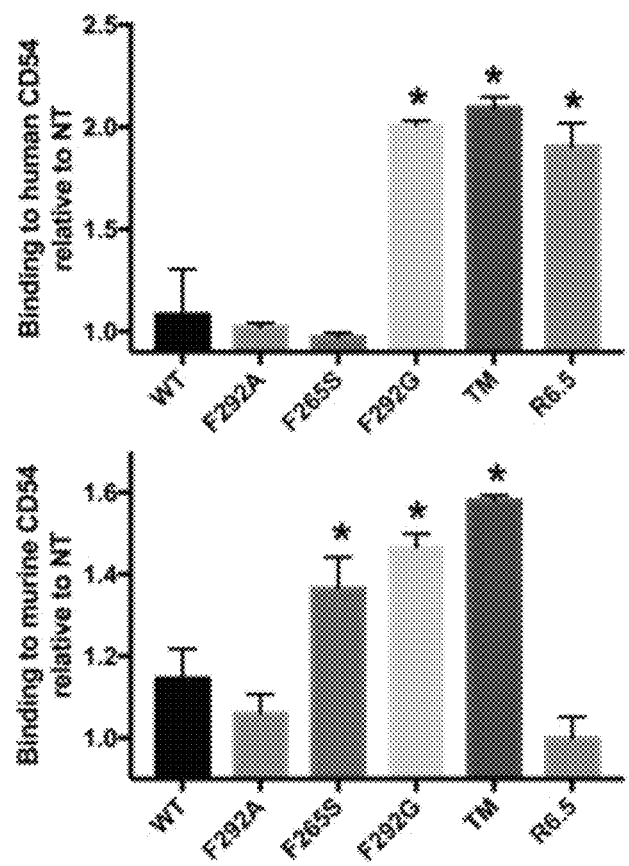

To test whether the mutant I domain affinities correlate with CAR affinities, HEK 293T and Jurkat T cells were transduced with lentivirus encoding $3^{rd}$ generation CARs containing TM, F292G, F292A, or WT I domain, and assayed for ICAM-1 binding. A myc tag was appended to the N-terminus of each I domain variant to aid measurement of CAR expression (FIGS. 1D-E). To avoid background ICAM-1 binding to endogenous LFA-1 in Jurkat T cells, CAR affinity for ICAM-1 was estimated using the I domain CAR-transduced HEK 293T cells. The level of recombinant human ICAM-1 binding to I domain CAR-expressing HEK 293T cells correlated with solution affinity measurements, with TM exhibiting the strongest binding, followed by F292G and F292A, and no detectable binding to WT compared to non-transduced (NT) T cells (FIG. 1F). Differential CAR affinities for ICAM-1 and cross-reactivity with murine ICAM-1 were also examined by measuring cell adhesion to V-bottom plates coated with recombinant human or murine ICAM-1 (FIG. 1G). Jurkat cells transduced with TM and F292G CARs demonstrated a higher level of binding to both human and murine ICAM-1 compared to non-transduced cells. However, despite increased binding of recombinant ICAM-1 to F292A CAR-expressing HEK 293T cells compared to their WT I domain-expressing counterparts (FIG. 1F), F292A CAR-Jurkat cells lacked any additional binding to plate-bound ICAM-1 compared to NT or WT I domain-expressing cells (FIG. 1G). In the case of F265S I domain, which demonstrated soluble ICAM-1-binding comparable to F292G (145 vs. 119 nM, Table 1), F265S CAR T cells failed to demonstrate any additional binding to plate-bound human ICAM-1 while elevated binding was more apparent to murine ICAM-1. As anticipated, T cells transduced to express R6.5 CAR, which is specific to human ICAM-1 only, exhibited elevated binding to human but not to murine ICAM-1 (FIG. 1G).

Example 14. Influence of CAR Affinity and Target Antigen Density on CAR T Cell Activation in vitro Jurkat T cells expressing I domain CARs were used to examine the extent to which CAR T cell activation was influenced by CAR affinity and ICAM-1 antigen density in target cells. Jurkat T cells were incubated with various target cell lines with different ICAM-1 expression levels. ICAM-1 surface densities of target cell lines were estimated by first assaying the levels of anti-ICAM-1 antibody binding to them and comparing these signals to those obtained using 8 µm latex beads coupled with known amounts of R6.5 antibody conjugated with cy5.5 ($10^3$-$10^7$ antibodies per bead). The level of shift after incubation with R6.5 (black) from non-labeled (grey) was used to estimate ICAM-1 density in each indicated target cell line.

The panel of target cells include: HMEC-1 and bEnd.3, representing, respectively, healthy human and mouse cells with physiological levels of ICAM-1 (~$10^4$ molecules per cell); anaplastic thyroid carcinoma (8505C) expressing an intermediate level (~$10^5$ per cell); and cervical cancer (HeLa) cell lines expressing a high level of ICAM-1 (~$10^6$ per cell). For additional comparisons, we included 8505C with CRISPR/Cas9-mediated ICAM-1 gene inactivation (8505C/-ICAM-1) and 8505C treated with LPS to upregulate ICAM-1 expression (8505C/LPS). Table 3 summarizes ICAM-1 site density in target cells used herein

TABLE 3

| Target cells | ICAM-1 density (molecules/cell) |
| --- | --- |
| bEND.3 | <$10^4$ |
| HMEC-1 | <$10^4$ |
| 8505C | $10^5$ |
| 8505C/LPS | $10^5$-$10^6$ |
| 8505C/-ICAM-1 | Non-detectable |
| HeLa | $10^6$ |

Activation of CAR T cells upon interaction with target cells was examined by measuring CD25 (IL-2 receptor α) and CD69 expression. CD25 expression in Jurkat CAR T cells (WT, F292A, F292G, and TM) were examined after co-incubation with different target cell lines for 24 h (n=3-4). CD69 was induced after incubation with latex beads coated with $10^6$ recombinant human ICAM-1-Fc molecules. Elevated levels of CD25 were observed in WT I domain CAR T cells following incubation with LPS-stimulated 8505C but not with other cell lines expressing lower levels of ICAM-1. In contrast, increased CD25 expression was seen when high affinity TM CAR T cells were incubated with high ICAM-1 expressing cells as well as with HMEC-1 and bEnd.3 cells expressing basal levels of ICAM-1. A low-level of CD25 expression was detected on TM CAR T cells following incubation with target cells lacking ICAM-1 expression (8505C/-ICAM-1), likely due to homotypic cellular contacts mediated by molecular interactions between TM CAR and basal expression of ICAM-1 on Jurkat cells (~$10^4$ molecules/cell). T cells expressing F292G behaved similar to TM, except that CD25 expression was close to background levels following co-incubation with 8505C/-ICAM-1. The micromolar affinity F292A T cells demonstrated selective activation displaying elevated CD25 expression only upon incubation with 8505C and 8505C/LPS cells. This indicates that a threshold target antigen density of >$10^5$ ICAM-1 molecules per cell was required for F292A CAR T cell activation. In contrast to the ICAM-1 density-dependent activation of CD25, increased CD69 expression was observed even in the absence of target cells, with expression levels aligning closely with CAR affinity to ICAM-1, which was not further enhanced by incubation with ICAM-1 coated latex beads. Compared to CD25, CD69 induction appeared to require a lower level threshold of antigen density for activation, which was provided by homotypic interaction between CAR T cells.

Figure 2A:
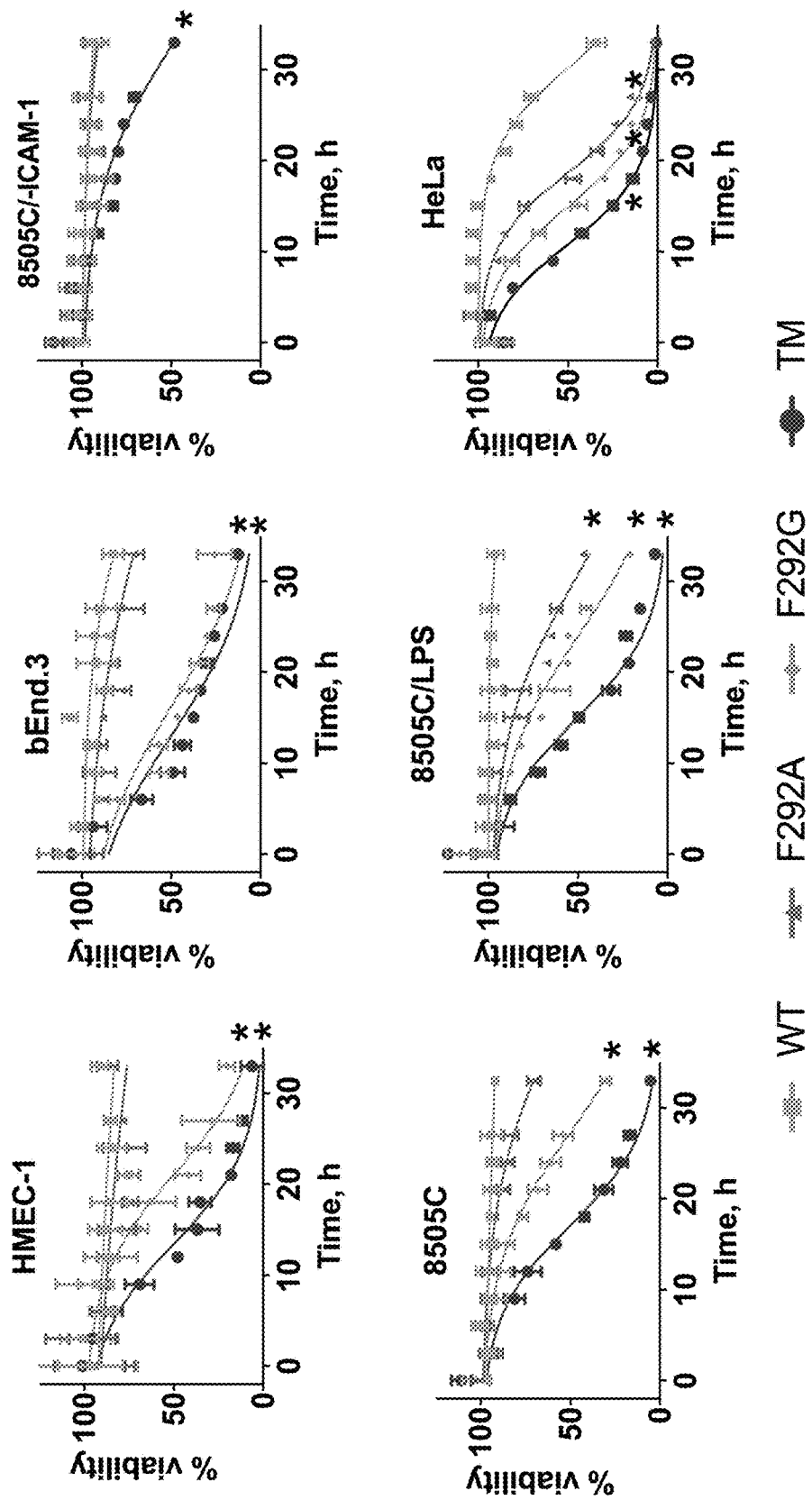
FIGS. 2A-2D show affinity and antigen-density dependent activation of primary CAR T cells in vitro.

Example 15. Influence of CAR Affinity and Target Antigen Density on CAR T Cell Cytotoxicity in vitro After validating affinity and antigen-dependent activation of CAR-modified Jurkat T cells, we sought to examine the influence of CAR affinity and antigen density on primary T cell activation and cytotoxicity in vitro. Primary T cells were transduced with TM, F292A, F292G, and WT I domain CARs, and added to various target cells to determine their cytotoxic efficacy in vitro. Overall, there was a positive correlation between the rate of target cell lysis and ICAM-1 expression (HeLa>8505C/LPS>8505C>HMEC-1>bEND.3) across all I domain variant CAR T cells (FIG. 2A). The rate of killing was also faster when T cells expressed CARs possessing higher affinity for ICAM-1 (TM>F292G>F292A>WT).

Figure 2B:
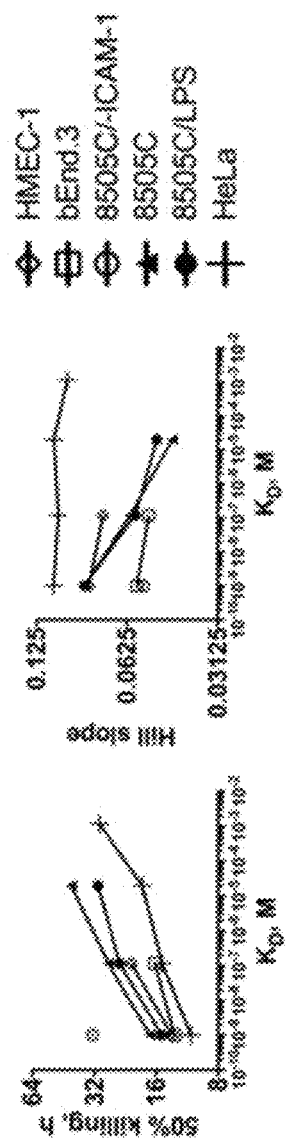
Figure 2C:
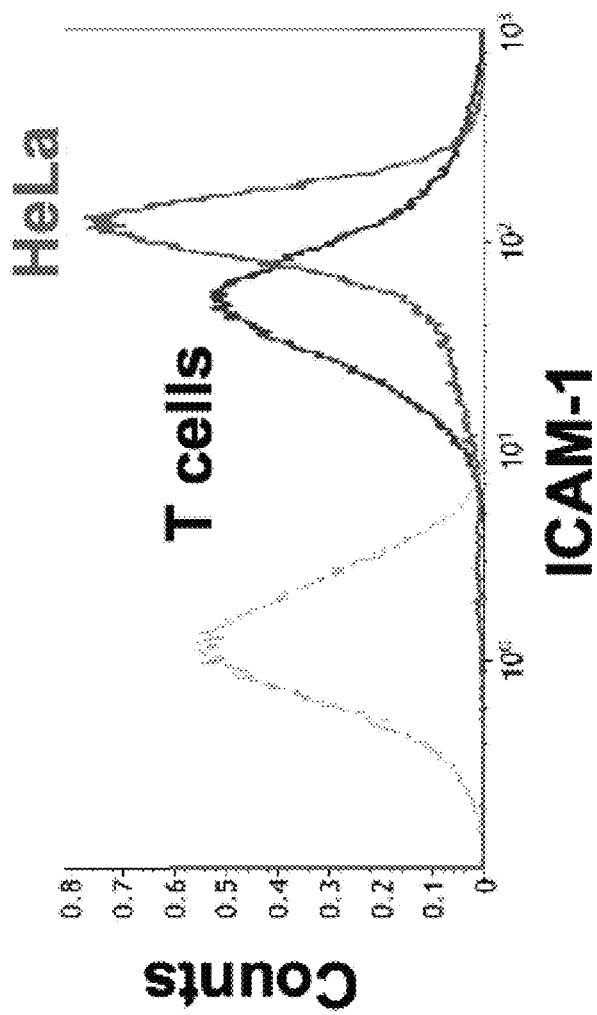

To quantitatively compare the efficacy of killing by affinity variant CAR T cells, a variable slope sigmoidal curve (% live=100/[1+$10^{(t-\tau\_50\%)*Slope}$]) was used to find the best fit values describing the time required to achieve 50% killing ($\tau\_50\%$) and the Hill slope (FIG. 2B). The time to 50% target killing was longer with either lower affinity CAR T cells or lower antigen density for the same CAR T cells. The Hill slope, corresponding to the rate of target killing by CAR T cells, was higher with increases in affinity (lower Kd) for the same target cells. The Hill slope was also greater with increases in antigen density for the same CAR T cells. CAR T cell killing of target cells was specific as evidenced by the lack of observed killing of ICAM-1 negative 8505C cells by all of I domain variant CARs except TM. Low yet gradual killing of 8505C/-ICAM-1 by TM T cells was likely due to cytotoxic activation caused by homotypic cellular contacts mediated by TM interaction with ICAM-1 in T cells. Table 4 summarizes time (hours) to 50% killing determined by fitting data to a variable slope sigmoidal curve.

TABLE 4

| CAR T | HMEC | bEND3 | 8505C/—ICAM-1 | 8505C | 8505C/LPS | HeLa |
| --- | --- | --- | --- | --- | --- | --- |
| WT | n.d. | n.d. | n.d. | n.d. | n.d. | 30.23 |
| F292A | n.d. | n.d. | n.d. | 41.55 | 30.81 | 18.66 |
| F292G | 21.05 | 16.23 | n.d. | 27.32 | 23.98 | 14.93 |
| TM | 13.45 | 13.03 | 32.63 | 17.12 | 15.05 | 10.84 |

Only the best fit values with r-square values higher than 0.85 are shown; otherwise indicated as not-determined, n.d.

Table 5 shows Hill slope values determined by fitting data to a variable slope sigmoidal curve.

TABLE 5

| CAR T | HMEC | bEND3 | 8505C/—ICAM-1 | 8505C | 8505C/LPS | HeLa |
|---|---|---|---|---|---|---|
| WT | n.d. | n.d. | n.d. | n.d. | n.d. | 0.09894 |
| F292A | n.d. | n.d. | n.d. | 0.04424 | 0.04976 | 0.1096 |
| F292G | 0.07538 | 0.05292 | n.d. | 0.06098 | 0.05872 | 0.1059 |
| TM | 0.08384 | 0.05793 | 0.05493 | 0.08686 | 0.08695 | 0.1099 |

Only the best fit values with r-square values higher than 0.85 are shown; otherwise indicated as not-determined, n.d.

ICAM-1 expression in primary T cells can be induced after T cell activation such as by incubation with CD3/CD28 beads (~$10^5$ molecules/cell). In comparison, WT CAR T cells possessing millimolar affinity (Kd=1.5 mM) could specifically lyse HeLa cells only, indicating a threshold antigen density of approximately $10^6$ molecules per cell for ~1 mM Kd CART cells. Importantly, F292A and WT I domain CAR T cells (Kd>10 µM) were unreactive to human and murine healthy control cells, HMEC-1 and b.END3 (~$10^4$ per cell; FIG. 2A).

Figure 2D:
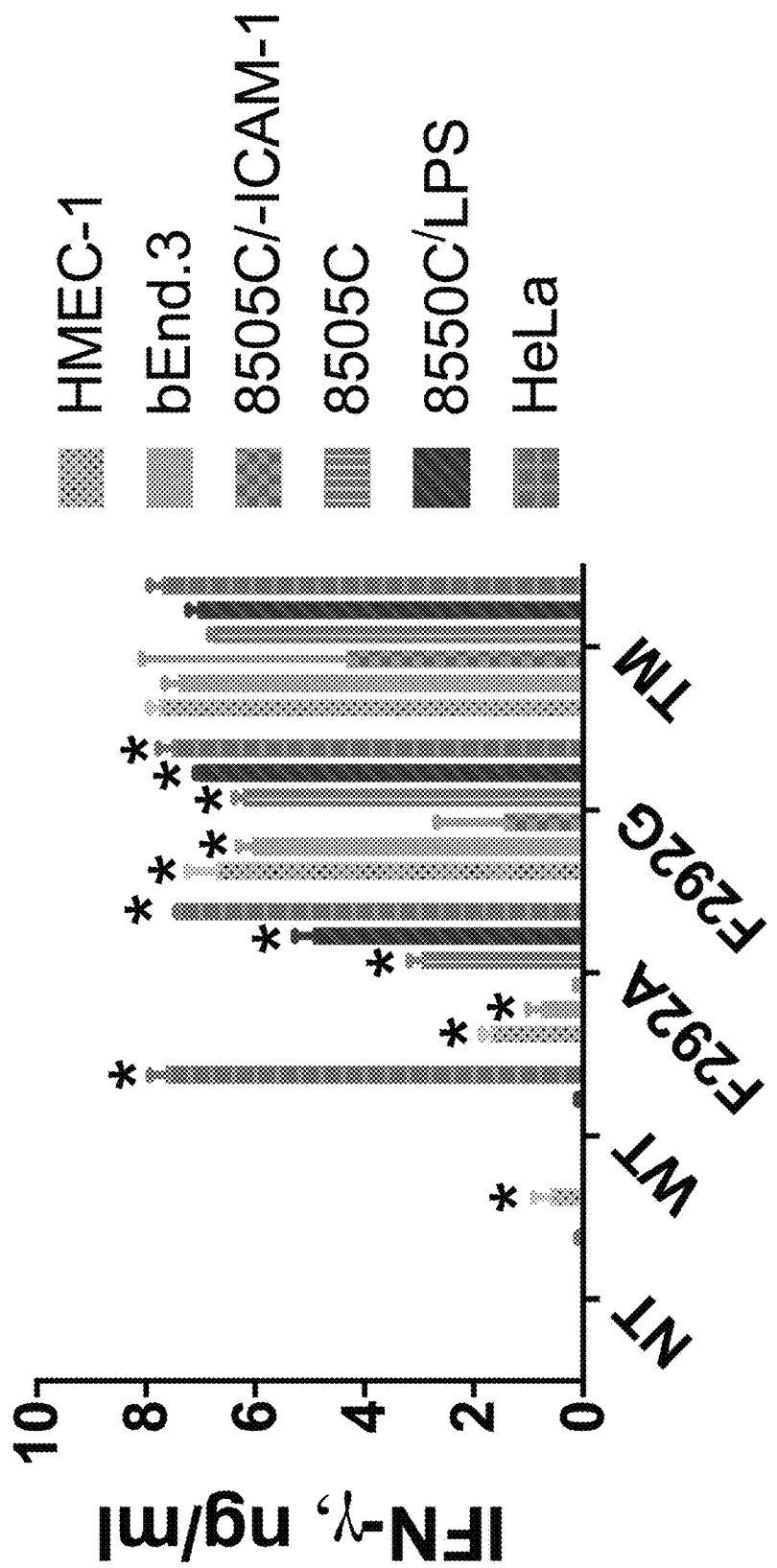

IFN-γ release by CAR T cells aligned closely with the rate of target cell death, where increasing levels were found in co-cultures containing higher affinity CAR T cells and/or higher levels of target antigen expression (FIG. 2D). One exception to target antigen density-dependent IFN-γ release was TM and F292G, which showed significant amounts of IFN-γ release (>1 ng/ml) in the absence of target molecules (8505C/-ICAM-1). This is again likely due to the homotypic interactions between T cells, which is also supported by the observation of the difficulty with expanding TM CAR T cells, particularly when the level of CAR expression was high. Release of IFN-γ by micromolar affinity CAR T cells (F292A) was in proportion to the ICAM-1 density in target cells, demonstrated by a lack of release upon incubation with 8505C/-ICAM-1, and progressively increasing with incubation with HMEC-1, 8505C, 8505C/LPS, and HeLa in this order (FIG. 2D). Consistent with WT I domain's cytotoxicity toward HeLa cells, IFN-γ release upon incubation with HeLa was comparable to the levels secreted by other higher affinity CAR T cells.

Example 16. In vivo Efficacy of Affinity-tuned I Domain CAR T Cells

Figure 3A:
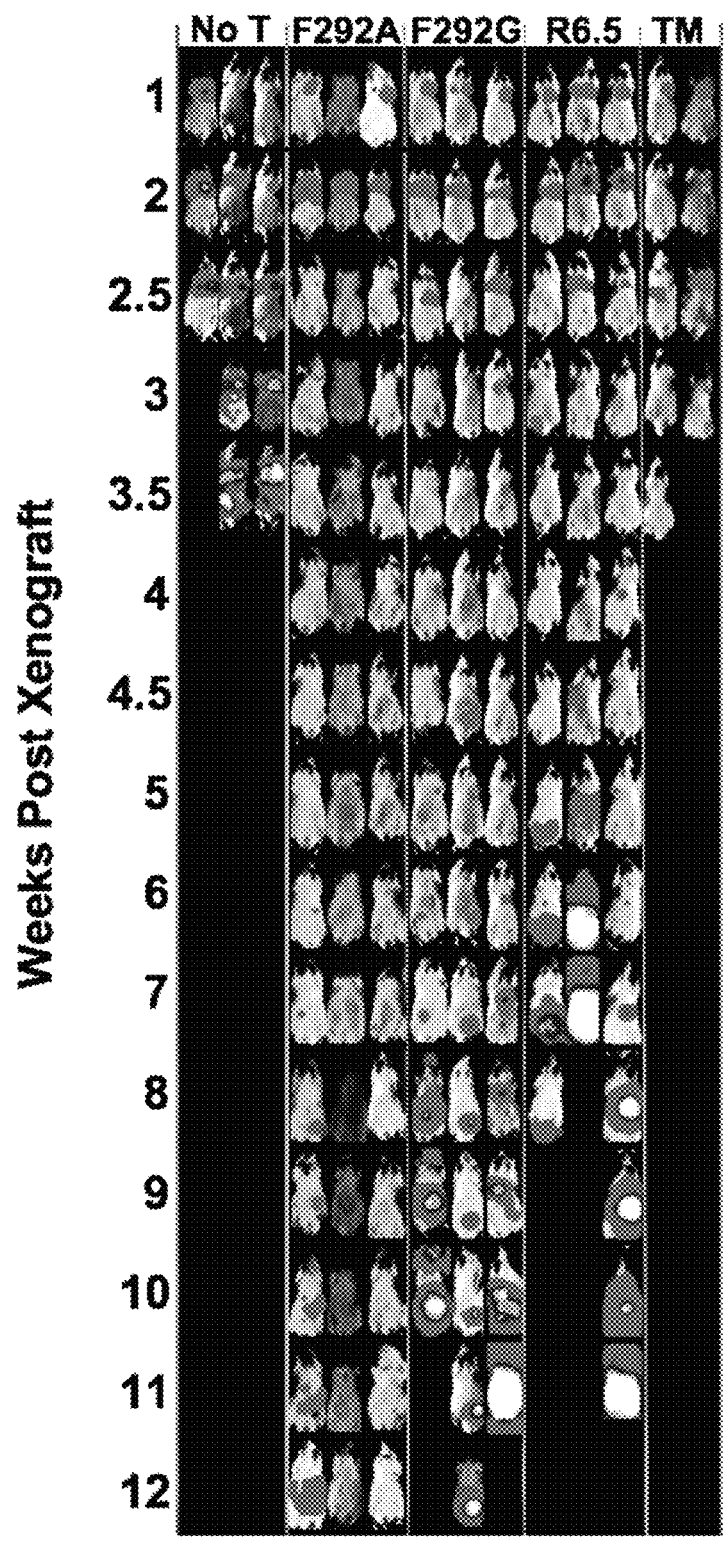
FIGS. 3A-3C show micromolar affinity CAR T cells provide superior tumor eradication, suppression of tumor relapse, and survival benefit.
Figure 3B:
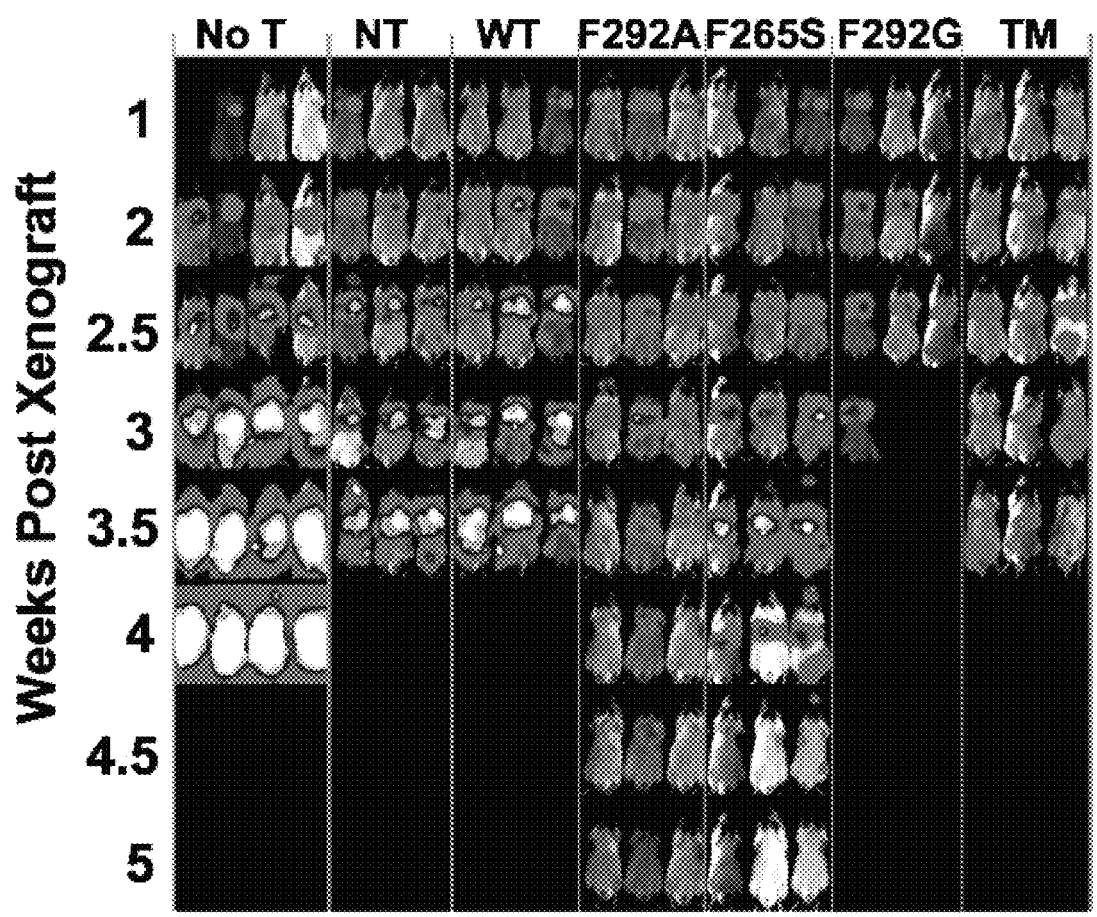

We examined how affinity-dependent CAR T cell cytotoxicity patterns in vitro would translate to tumor xenograft models in vivo. In solid tumors, CAR T cell efficacy is influenced by their ability to traffic to tumor sites, penetrate, serially lyse tumor cells, and undergo expansion and contraction in accordance with tumor burden. Here, mice were xenografted by systemic i.v. injections of $0.75 \times 10^6$ 8505C-FLuc+GFP+ cells followed by treatment with ~$1-3 \times 10^6$ I domain CAR T cells (WT, F292A, F265S, F292G, and TM), SSTR2-R6.5 CAR[29], NT (non-transduced) T cells, and no T cells at 8-10 days post-xenograft (5-20% CAR expression). Tumor burden was evaluated by whole-body luminescence imaging of firefly luciferase activity. Primary tumors localized to the lungs and liver with distant metastatic foci evident throughout the body (FIG. 3A). Cohorts receiving either no T cells or NT T cells succumbed to tumor burden within 3-4 weeks of tumor inoculation. Mice treated with TM CAR T cells displayed rapid initial reductions in tumor burden; however, at approximately 7 days post T cell injection, mice began to show symptoms of systemic toxicity indicated by lethargy and weight loss, resulting in death by day 15 post treatment (FIGS. 3A-B). F292G CAR T cells were capable of tumor elimination with inconsistent toxicity development, which appeared to be partially dependent on tumor burden at the time of CART cell treatment. For example, either delayed infusions of F292G (119 nM affinity) CAR T cells (day 10) or higher tumor burden at the time of treatment led to more frequent deaths. T cells expressing F265S (145 nM Kd) CARs, eliminated tumors without observable toxicity. This suggests that an I domain CAR affinity of ~100 nM Kd defines an approximate threshold affinity, above which (Kd less than 100 nM such 1-10 nM) treatment leads to reduced discrimination between high and low antigen densities and an increased likelihood of on-target off-tumor toxicity. Consistent with limited or lack of killing of 8505C by WT CAR T cells in vitro, tumor progression in vivo was unimpeded by the treatment of WT CAR T cells, similar to NT T cells (FIG. 3B). In contrast, F292A CAR T cells, which exhibited a much slower in vitro rate of 8505C killing compared to its higher affinity counterparts, achieved rapid reductions in tumor burden with no apparent toxicity irrespective of treatment timing (FIG. 3A-3B). Moreover, F292A CAR T in vivo efficacy was superior to the scFv-based R6.5 CAR despite >1,000-fold lower affinity to ICAM-1 (10 nM vs. 20 µM), as evidenced by a faster rate of tumor clearance and durable suppression of tumor relapse (FIG. 3A).

Figure 3C:
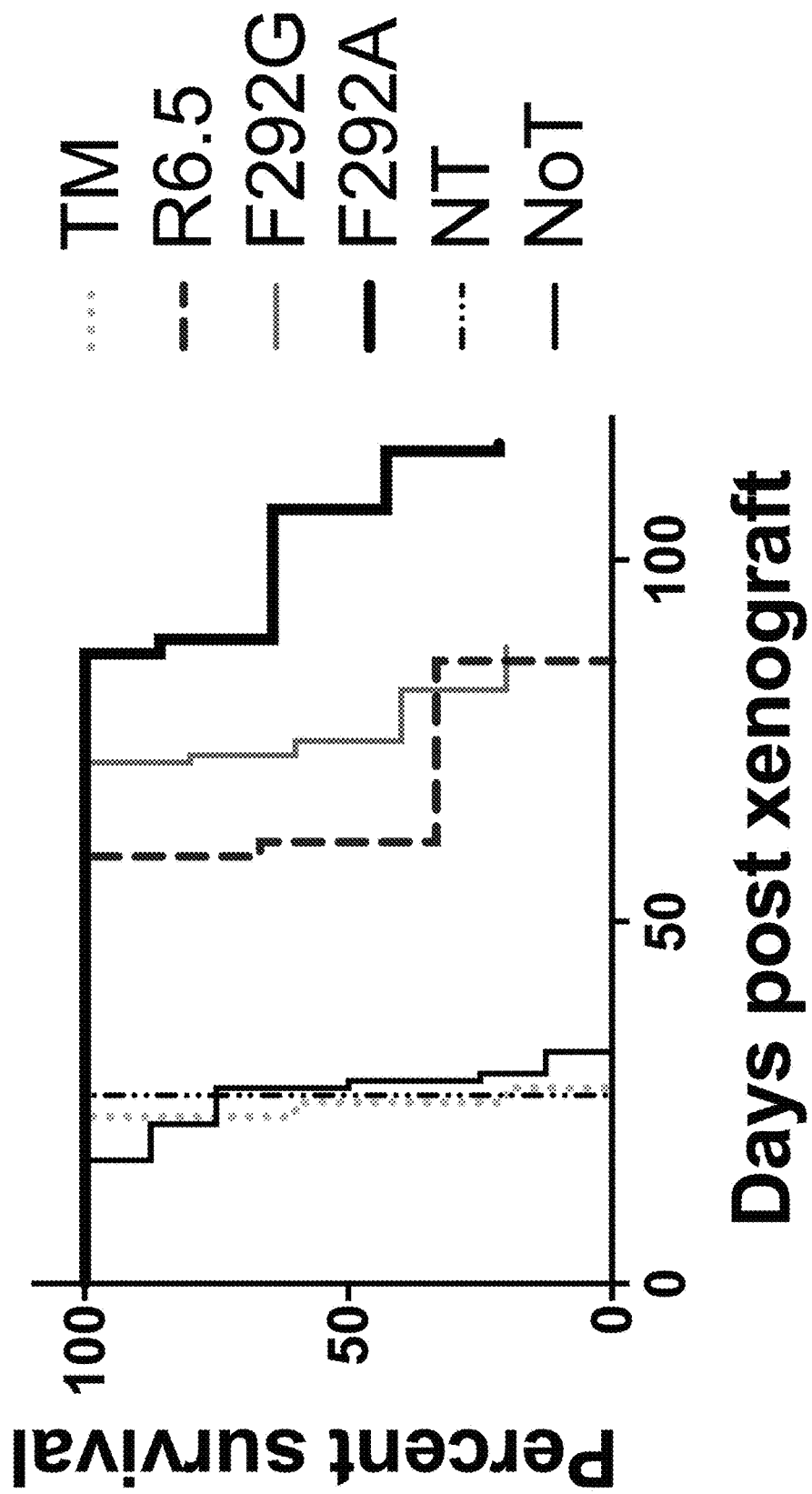

Overall, the anti-tumor efficacy of I domain CAR T cells led to statistically significant increases in cohort survival compared with no T or NT T cell treated mice (FIG. 3C). However, CAR T cell-treated mice even with no to little tumor burden began to show signs of toxicity (e.g., weight loss, loss of fur) that eventually led to frequent death ~10 weeks after T cell injections. This was suspected to be related to graft-versus-host disease[34] and not on-target, off-tumor toxicity as similar toxicities were observed in mice treated with R6.5 CAR T cells that exclusively target human ICAM-1.

Example 17. Real-time Imaging of CAR T Cell Kinetics, Efficacy, and Toxicity

Figure 4A:
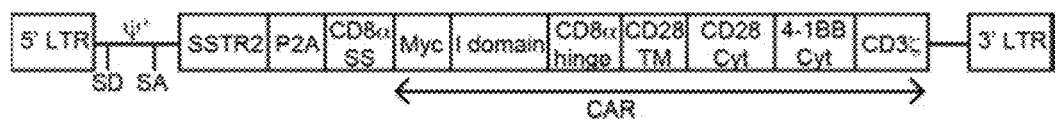
FIGS. 4A-4D show longitudinal, concurrent measurements of tumor burden, T cell distribution, and cytokine release.

To spatiotemporally monitor T cell distribution in real-time by PET/CT, we introduced an imaging reporter gene, SSTR2 into the I domain CAR vector using a ribosome skipping P2A sequence to ensure equal expression of CAR and the reporter on the surface of T cells (FIG. 4A). Expression of SSTR2 enabled binding and intracellular accumulation of an infused, positron-emitting, SSTR2-specific radiotracer, $^{18}$F-NOTA-Octreotide[30]. Emitted signals were then detected with high resolution with no tissue penetration issues by a micro PET scanner. Flow cytometry measurements of SSTR2 reporter gene and Myc-tag expression representing CAR on the surface of primary human T cells. Expression of SSTR2 and Myc tagged I domain was confirmed by antibody staining by flow cytometry measurements of SSTR2 reporter gene and Myc-tag expression representing CAR on the surface of primary human T cells.

Figure 4B:
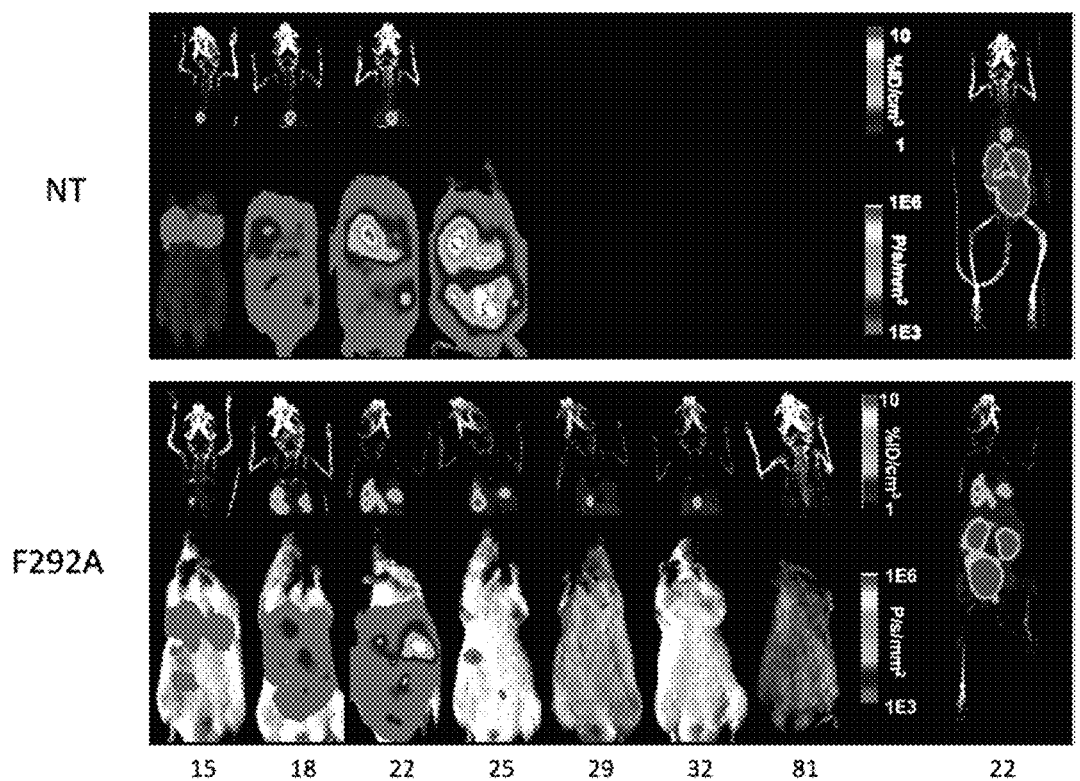
Figure 4C:
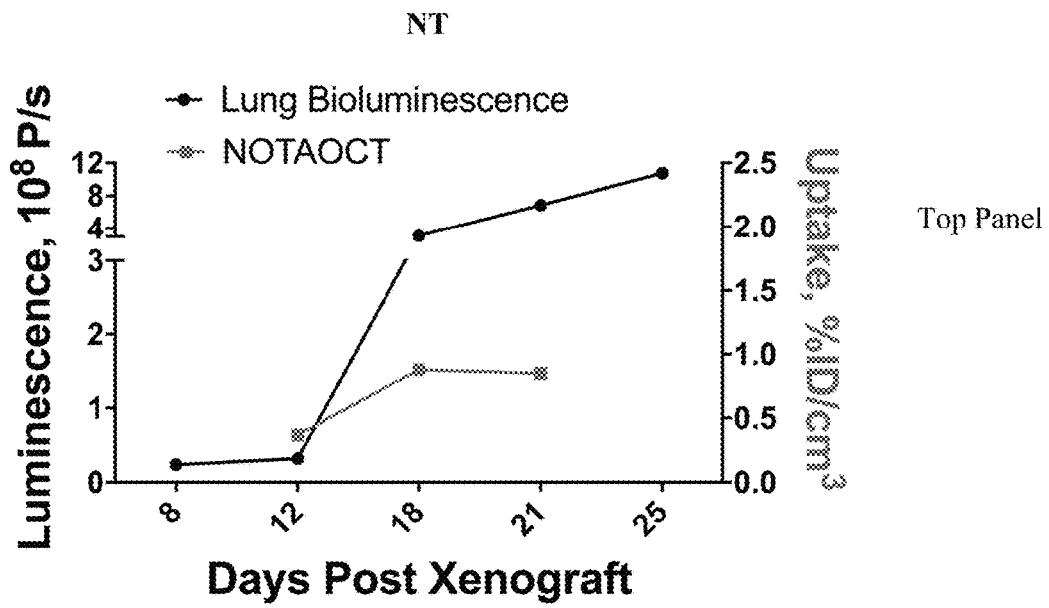
Figure 4C:
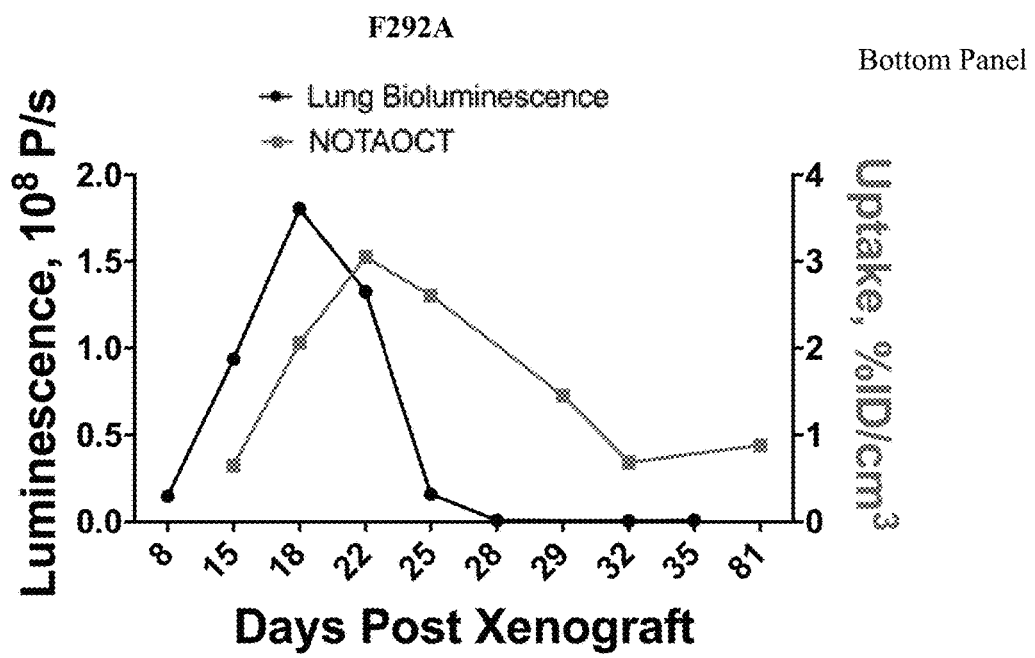

Mice were xenografted with 8505C tumors as before, and were treated with NT or F292A CAR T cells. Whole-body luminescence imaging was performed to estimate tumor burden while PET/CT imaging was performed on the same day to track CAR T cell distribution (FIG. 4B). At each time point, blood was collected to measure human cytokines for correlation with T cell dynamics. PET/CT images in mice displayed expected background levels in gall bladder, kidneys and bladder caused by radiotracer excretion (FIG. 4B; far-right). In the NT treated control cohort, a small but gradual increase in non-specific tracer uptake was observed, which was due to increasing tumor burden and the associated increase in blood pooling (FIG. 4B). In contrast, specific tracer uptake was observed in mice treated with SSTR2-F292A CAR T cells, demonstrating the expansion and contraction phases in the lungs, with peak CAR T cell signal occurring approximately at 22 days post xenograft, which is 4 days following peak tumor burden (18 days post xenograft), and gradually decreasing to background levels (FIGS. 4B-4C). This shows biphasic T cell expansion and contraction phenomenon.

Figure 4D:
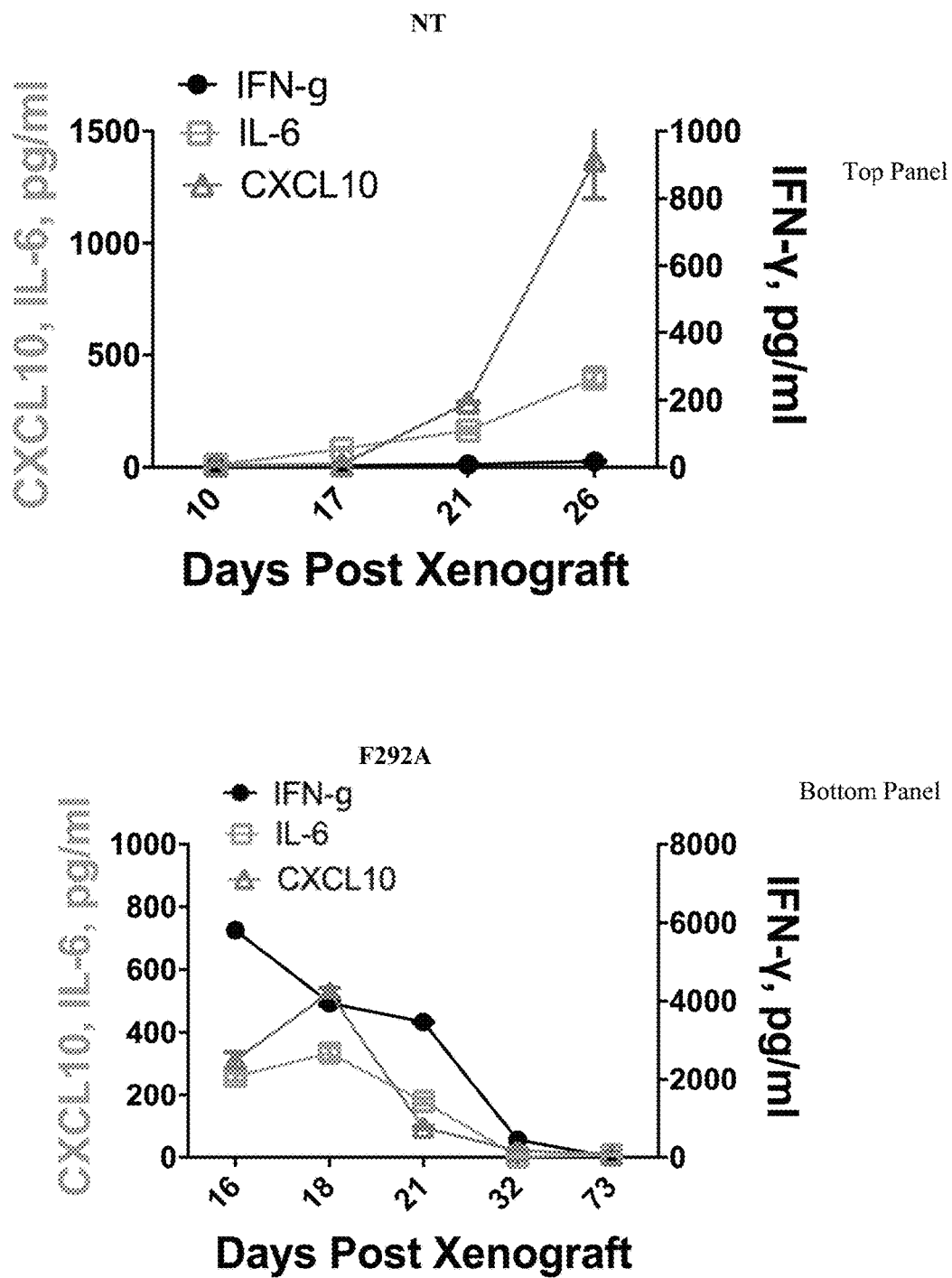

Cytokine analysis of serum obtained from treated mice demonstrated a surge in IFN-γ, IL-6, and CXCL10 concentrations prior to peak T cell expansion, which also returned to background levels post tumor elimination and following contraction of T cell density in the lungs to background levels (FIG. 4D).

REFERENCES

1. Maher J, Brentjens R J, Gunset G, Riviere I, Sadelain M. Human T-lymphocyte cytotoxicity and proliferation directed by a single chimeric TCRzeta/CD28 receptor. *Nat Biotechnol* 20, 70-75 (2002).
2. Gross G, Waks T, Eshhar Z. Expression of immunoglobulin-T-cell receptor chimeric molecules as functional receptors with antibody-type specificity. *Proc Natl Acad Sci USA* 86, 10024-10028 (1989).
3. Hudecek M, et al. Receptor affinity and extracellular domain modifications affect tumor recognition by ROR1-specific chimeric antigen receptor T cells. *Clin Cancer Res* 19, 3153-3164 (2013).
4. Watanabe K, et al. Target antigen density governs the efficacy of anti-CD20-CD28-CD3 zeta chimeric antigen receptor-modified effector CD8+ T cells. *J Immunol* 194, 911-920 (2015).
5. Kochenderfer J N, et al. Eradication of B-lineage cells and regression of lymphoma in a patient treated with autologous T cells genetically engineered to recognize CD19. *Blood* 116, 4099-4102 (2010).
6. Porter D L, Levine B L, Kalos M, Bagg A, June C H. Chimeric antigen receptor-modified T cells in chronic lymphoid leukemia. *New England Journal of Medicine* 365, 725-733 (2011).
7. Grupp S A, et al. Chimeric antigen receptor-modified T cells for acute lymphoid leukemia. *N Engl J Med* 368, 1509-1518 (2013).
8. Brentjens R J, et al. CD19-targeted T cells rapidly induce molecular remissions in adults with chemotherapy-refractory acute lymphoblastic leukemia. *Sci Transl Med* 5, 177ra138 (2013).
9. Brudno J N, Kochenderfer J N. Toxicities of chimeric antigen receptor T cells: recognition and management. *Blood* 127, 3321-3330 (2016).
10. Cheever M A, et al. The prioritization of cancer antigens: a national cancer institute pilot project for the acceleration of translational research. *Clin Cancer Res* 15, 5323-5337 (2009).
11. Kakarla S, Gottschalk S. CAR T cells for solid tumors: armed and ready to go? *Cancer J* 20, 151-155 (2014).
12. Lamers C H, et al. Treatment of metastatic renal cell carcinoma with autologous T-lymphocytes genetically retargeted against carbonic anhydrase IX: first clinical experience. *J Clin Oncol* 24, e20-22 (2006).
13. Parkhurst M R, et al. T cells targeting carcinoembryonic antigen can mediate regression of metastatic colorectal cancer but induce severe transient colitis. *Mol Ther* 19, 620-626 (2011).
14. Morgan R A, Yang J C, Kitano M, Dudley M E, Laurencot C M, Rosenberg S A. Case report of a serious adverse event following the administration of T cells transduced with a chimeric antigen receptor recognizing ERBB2. *Mol Ther* 18, 843-851 (2010).
15. Tian S, Maile R, Collins E J, Frelinger J A. CD8+ T cell activation is governed by TCR-peptide/MHC affinity, not dissociation rate. *J Immunol* 179, 2952-2960 (2007).
16. Hebeisen M, Allard M, Gannon P O, Schmidt J, Speiser D E, Rufer N. Identifying Individual T Cell Receptors of Optimal Avidity for Tumor Antigens. *Front Immunol* 6, 582 (2015).
17. Zhong S, et al. T-cell receptor affinity and avidity defines antitumor response and autoimmunity in T-cell immunotherapy. *Proc Natl Acad Sci USA* 110, 6973-6978 (2013).
18. Liu X, et al. Affinity-Tuned ErbB2 or EGFR Chimeric Antigen Receptor T Cells Exhibit an Increased Therapeutic Index against Tumors in Mice. *Cancer Res* 75, 3596-3607 (2015).
19. Caruso H G, et al. Tuning Sensitivity of CAR to EGFR Density Limits Recognition of Normal Tissue While Maintaining Potent Antitumor Activity. *Cancer Res* 75, 3505-3518 (2015).
20. Arcangeli S, et al. Balance of Anti-CD123 Chimeric Antigen Receptor Binding Affinity and Density for the Targeting of Acute Myeloid Leukemia. *Mol Ther*, (2017).
21. Chmielewski M, Hombach A, Heuser C, Adams G P, Abken H. T cell activation by antibody-like immunoreceptors: increase in affinity of the single-chain fragment domain above threshold does not increase T cell activation against antigen-positive target cells but decreases selectivity. *J Immunol* 173, 7647-7653 (2004).
22. Schmid D A, et al. Evidence for a TCR affinity threshold delimiting maximal CD8 T cell function. *J Immunol* 184, 4936-4946 (2010).
23. Corse E, Gottschalk R A, Krogsgaard M, Allison J P. Attenuated T cell responses to a high-potency ligand in vivo. *PLoS Biol* 8, (2010).
24. Park S, et al. Tumor suppression via paclitaxel-loaded drug carriers that target inflammation marker upregulated in tumor vasculature and macrophages. *Biomaterials* 34, 598-605 (2013).
25. Dustin M L, Rothlein R, Bhan A K, Dinarello C A, Springer T A. Induction by IL 1 and interferon-gamma: tissue distribution, biochemistry, and function of a natural adherence molecule (ICAM-1). *J Immunol* 137, 245-254 (1986).
26. Shimaoka M, et al. Reversibly locking a protein fold in an active conformation with a disulfide bond: integrin alphaL I domains with high affinity and antagonist activity in vivo. *Proc Natl Acad Sci USA* 98, 6009-6014 (2001).
27. Jin M, et al. Directed evolution to probe protein allostery and integrin I domains of 200,000-fold higher affinity. *Proc Natl Acad Sci USA* 103, 5758-5763 (2006).
28. Wong R, Chen X, Wang Y, Hu X, Jin M M. Visualizing and Quantifying Acute Inflammation Using ICAM-1 Specific Nanoparticles and MRI Quantitative Susceptibility Mapping. *Ann Biomed Eng* 40, 1328-1338 (2011).
29. Vedvyas Y, et al. Longitudinal PET imaging demonstrates biphasic CAR T cell responses in survivors. *JCI Insight* 1, e90064 (2016).
30. Laverman P, et al. A novel facile method of labeling octreotide with (18)F-fluorine. *J Nucl Med* 51, 454-461 (2010).
31. McBride W J, et al. A novel method of 18F radiolabeling for PET. *J Nucl Med* 50, 991-998 (2009).

32. Kinahan P E, Fletcher J W. Positron emission tomography-computed tomography standardized uptake values in clinical practice and assessing response to therapy. *Semin Ultrasound CT MR* 31, 496-505 (2010).
33. Leelawattanachai J, Kwon K W, Michael P, Ting R, Kim J Y, Jin M M. Side-by-Side Comparison of Commonly Used Biomolecules That Differ in Size and Affinity on Tumor Uptake and Internalization. *PLoS One* 10, e0124440 (2015).
34. Poirot L, et al. Multiplex Genome-Edited T-cell Manufacturing Platform for "Off-the-Shelf" Adoptive T-cell Immunotherapies. *Cancer Res* 75, 3853-3864 (2015).
35. Kang S, et al. Virus-mimetic polyplex particles for systemic and inflammation-specific targeted delivery of large genetic contents. *Gene Ther* 20, 1042-1052 (2013).
36. Hinrichs C S, Restifo N P. Reassessing target antigens for adoptive T-cell therapy. *Nat Biotechnol* 31, 999-1008 (2013).
37. Newick K, O'Brien S, Moon E, Albelda S M. CAR T Cell Therapy for Solid Tumors. *Annu Rev Med* 68, 139-152 (2017).
38. Ledebur H C, Parks T P. Transcriptional regulation of the intercellular adhesion molecule-1 gene by inflammatory cytokines in human endothelial cells. Essential roles of a variant NF-kappa B site and p65 homodimers. *J Biol Chem* 270, 933-943 (1995).
39. Usami Y, et al. Intercellular adhesion molecule-1 (ICAM-1) expression correlates with oral cancer progression and induces macrophage/cancer cell adhesion. *Int J Cancer* 133, 568-578 (2013).
40. Roland C L, Harken A H, Sarr M G, Barnett C C, Jr. ICAM-1 expression determines malignant potential of cancer. *Surgery* 141, 705-707 (2007).
41. Guo P, et al. ICAM-1 as a molecular target for triple negative breast cancer. *Proc Natl Acad Sci USA* 111, 14710-14715 (2014).
42. Carman C V, Springer T A. Integrin avidity regulation: are changes in affinity and conformation underemphasized? *Curr Opin Cell Biol* 15, 547-556 (2003).
43. Boissonnas A, Fetler L, Zeelenberg I S, Hugues S, Amigorena S. In vivo imaging of cytotoxic T cell infiltration and elimination of a solid tumor. *J Exp Med* 204, 345-356 (2007).
44. Porter B B, Harty J T. The onset of CD8+-T-cell contraction is influenced by the peak of *Listeria monocytogenes* infection and antigen display. *Infect Immun* 74, 1528-1536 (2006).
45. Keu K V, et al. Reporter gene imaging of targeted T cell immunotherapy in recurrent glioma. *Sci Transl Med* 9, (2017).
46. Yaghoubi S S, et al. Noninvasive detection of therapeutic cytolytic T cells with 18F-FHBG PET in a patient with glioma. *Nat Clin Pract Oncol* 6, 53-58 (2009).
47. Drent E, et al. A Rational Strategy for Reducing On-Target Off-Tumor Effects of CD38-Chimeric Antigen Receptors by Affinity Optimization. *Mol Ther*, (2017).
48. Kalergis A M, et al. Efficient T cell activation requires an optimal dwell-time of interaction between the TCR and the pMHC complex. *Nat Immunol* 2, 229-234 (2001).
49. Valitutti S. The Serial Engagement Model 17 Years After: From TCR Triggering to Immunotherapy. *Front Immunol* 3, 272 (2012).
50. McMahan R H, McWilliams J A, Jordan K R, Dow S W, Wilson D B, Slansky J E. Relating TCR-peptide-MHC affinity to immunogenicity for the design of tumor vaccines. *The Journal of clinical investigation* 116, 2543-2551 (2006).
51. Robbins P F, et al. Single and dual amino acid substitutions in TCR CDRs can enhance antigen-specific T cell functions. *J Immunol* 180, 6116-6131 (2008).
52. Co M S, Deschamps M, Whitley R J, Queen C. Humanized antibodies for antiviral therapy. *Proc Natl Acad Sci USA* 88, 2869-2873 (1991).
53. Leelawattanachai J, Kwon K-W, Michael P, Ting R, Kim J-Y, Jin M M. Side-by-Side Comparison of Commonly Used Biomolecules That Differ in Size and Affinity on Tumor Uptake and Internalization. *PLoS One* 10, e0124440 (2015).
54. Jin M, et al. Directed evolution to probe protein allostery and integrin I domains of 200,000-fold higher affinity. *Proc Natl Acad Sci USA* 103, 5758-5763 (2006).
55. Wong R, Chen X, Wang Y, Hu X, Jin M M. Visualizing and quantifying acute inflammation using ICAM-1 specific nanoparticles and MRI quantitative susceptibility mapping. *Ann Biomed Eng* 40, 1328-1338 (2012).

What is claimed is:

1. A Chimeric antigen receptor (CAR) comprising from N-terminus to C-terminus:
   (i) an I domain of the $\alpha_L$ subunit of human lymphocyte function-associated antigen-1,
   (ii) a transmembrane domain,
   (iii) at least one co-stimulatory domains, and
   (iv) an activating domain, wherein the I domain binds ICAM-1 at an affinity between about 145 nM to about 20 μM, and the I domain comprises the sequence of 130-310 amino acids of SEQ ID NO: 1, with one mutation of F292A, F292S, L289G, or F265S.

2. The CAR according to claim 1, wherein the co-stimulatory domain is selected from the group consisting of CD28, 4-1BB, ICOS-1, CD27, OX-40, GITR, and DAP10.

3. The CAR according to claim 1, wherein the activating domain is CD3 zeta.

4. An isolated nucleic acid encoding the CAR of claim 1.

5. T cells or natural killer cells modified to express the CAR of claim 1.

6. An adoptive cell therapy method for treating cancer, comprising the steps of:
   obtaining CAR-T cells expressing a chimeric antigen receptor (CAR) comprising from N-terminus to C-terminus:
   (i) an I domain of the $\alpha_L$ subunit of human lymphocyte function-associated antigen-1,
   (ii) a transmembrane domain,
   (iii) at least one co-stimulatory domains, and
   (iv) an activating domain, wherein the I domain binds ICAM-1 at an affinity between about 145 nm to about 20 μM, and the I domain comprises the sequence of 130-310 amino acids of SEQ ID NO: 1, with one mutation of F292A, F292S, L289G, or F265S,
   administering the CAR-T cells to a subject suffering from cancer, wherein the cancer cells of the subject overexpress ICAM-1, and the CAR T cells bind to the cancer cells to kill the cancer cells.

7. The method according to claim 6, wherein the cancer is thyroid cancer, gastric cancer, pancreatic cancer, or breast cancer.

8. The method according to claim 6, wherein the one mutation is F292A.

9. The method according to claim 6, wherein the co-stimulatory domain is selected from the group consisting of CD28, 4-1BB, ICOS-1, CD27, OX-40, GITR, and DAP10.

10. The method according to claim 6, wherein the co-stimulatory domain comprises CD28 and 4-1BB.

11. The CAR according to claim 6, wherein the activating domain is CD3 zeta.

12. The CAR according to claim 1, wherein the one mutation is F292A.

13. The CAR according to claim 1, wherein the co-stimulatory domain comprises CD28 and 4-1BB.

* * * * *

SEQUENCE LISTING

```
<160> NUMBER OF SEQ ID NOS: 1

<210> SEQ ID NO 1
<211> LENGTH: 1145
<212> TYPE: PRT
<213> ORGANISM: Homo sapiens

<400> SEQUENCE: 1

Tyr Asn Leu Asp Val Arg Gly Ala Arg Ser Phe Ser Pro Pro Arg Ala
1               5                   10                  15

Gly Arg His Phe Gly Tyr Arg Val Leu Gln Val Gly Asn Gly Val Ile
            20                  25                  30

Val Gly Ala Pro Gly Glu Gly Asn Ser Thr Gly Ser Leu Tyr Gln Cys
        35                  40                  45

Gln Ser Gly Thr Gly His Cys Leu Pro Val Thr Leu Arg Gly Ser Asn
    50                  55                  60

Tyr Thr Ser Lys Tyr Leu Gly Met Thr Leu Ala Thr Asp Pro Thr Asp
65                  70                  75                  80
```

-continued

Gly Ser Ile Leu Ala Cys Asp Pro Gly Leu Ser Arg Thr Cys Asp Gln
            85                  90                  95

Asn Thr Tyr Leu Ser Gly Leu Cys Tyr Leu Phe Arg Gln Asn Leu Gln
            100                 105                 110

Gly Pro Met Leu Gln Gly Arg Pro Gly Phe Gln Glu Cys Ile Lys Gly
            115                 120                 125

Asn Val Asp Leu Val Phe Leu Phe Asp Gly Ser Met Ser Leu Gln Pro
130                 135                 140

Asp Glu Phe Gln Lys Ile Leu Asp Phe Met Lys Asp Val Met Lys Lys
145                 150                 155                 160

Leu Ser Asn Thr Ser Tyr Gln Phe Ala Ala Val Gln Phe Ser Thr Ser
                165                 170                 175

Tyr Lys Thr Glu Phe Asp Phe Ser Asp Tyr Val Lys Trp Lys Asp Pro
            180                 185                 190

Asp Ala Leu Leu Lys His Val Lys His Met Leu Leu Leu Thr Asn Thr
            195                 200                 205

Phe Gly Ala Ile Asn Tyr Val Ala Thr Glu Val Phe Arg Glu Glu Leu
            210                 215                 220

Gly Ala Arg Pro Asp Ala Thr Lys Val Leu Ile Ile Ile Thr Asp Gly
225                 230                 235                 240

Glu Ala Thr Asp Ser Gly Asn Ile Asp Ala Ala Lys Asp Ile Ile Arg
                245                 250                 255

Tyr Ile Ile Gly Ile Gly Lys His Phe Gln Thr Lys Glu Ser Gln Glu
            260                 265                 270

Thr Leu His Lys Phe Ala Ser Lys Pro Ala Ser Glu Phe Val Lys Ile
            275                 280                 285

Leu Asp Thr Phe Glu Lys Leu Lys Asp Leu Phe Thr Glu Leu Gln Lys
            290                 295                 300

Lys Ile Tyr Val Ile Glu Gly Thr Ser Lys Gln Asp Leu Thr Ser Phe
305                 310                 315                 320

Asn Met Glu Leu Ser Ser Ser Gly Ile Ser Ala Asp Leu Ser Arg Gly
                325                 330                 335

His Ala Val Val Gly Ala Val Gly Ala Lys Asp Trp Ala Gly Gly Phe
            340                 345                 350

Leu Asp Leu Lys Ala Asp Leu Gln Asp Asp Thr Phe Ile Gly Asn Glu
            355                 360                 365

Pro Leu Thr Pro Glu Val Arg Ala Gly Tyr Leu Gly Tyr Thr Val Thr
            370                 375                 380

Trp Leu Pro Ser Arg Gln Lys Thr Ser Leu Leu Ala Ser Gly Ala Pro
385                 390                 395                 400

Arg Tyr Gln His Met Gly Arg Val Leu Leu Phe Gln Glu Pro Gln Gly
                405                 410                 415

Gly Gly His Trp Ser Gln Val Gln Thr Ile His Gly Thr Gln Ile Gly
            420                 425                 430

Ser Tyr Phe Gly Gly Glu Leu Cys Gly Val Asp Val Asp Gln Asp Gly
            435                 440                 445

Glu Thr Glu Leu Leu Leu Ile Gly Ala Pro Leu Phe Tyr Gly Glu Gln
            450                 455                 460

Arg Gly Gly Arg Val Phe Ile Tyr Gln Arg Arg Gln Leu Gly Phe Glu
465                 470                 475                 480

Glu Val Ser Glu Leu Gln Gly Asp Pro Gly Tyr Pro Leu Gly Arg Phe
                485                 490                 495

Gly Glu Ala Ile Thr Ala Leu Thr Asp Ile Asn Gly Asp Gly Leu Val

```
                500                 505                 510
Asp Val Ala Val Gly Ala Pro Leu Glu Glu Gln Gly Ala Val Tyr Ile
                515                 520                 525
Phe Asn Gly Arg His Gly Gly Leu Ser Pro Gln Pro Ser Gln Arg Ile
                530                 535                 540
Glu Gly Thr Gln Val Leu Ser Gly Ile Gln Trp Phe Gly Arg Ser Ile
545                 550                 555                 560
His Gly Val Lys Asp Leu Glu Gly Asp Gly Leu Ala Asp Val Ala Val
                565                 570                 575
Gly Ala Glu Ser Gln Met Ile Val Leu Ser Ser Arg Pro Val Val Asp
                580                 585                 590
Met Val Thr Leu Met Ser Phe Ser Pro Ala Glu Ile Pro Val His Glu
                595                 600                 605
Val Glu Cys Ser Tyr Ser Thr Ser Asn Lys Met Lys Glu Gly Val Asn
                610                 615                 620
Ile Thr Ile Cys Phe Gln Ile Lys Ser Leu Tyr Pro Gln Phe Gln Gly
625                 630                 635                 640
Arg Leu Val Ala Asn Leu Thr Tyr Thr Leu Gln Leu Asp Gly His Arg
                645                 650                 655
Thr Arg Arg Arg Gly Leu Phe Pro Gly Gly Arg His Glu Leu Arg Arg
                660                 665                 670
Asn Ile Ala Val Thr Thr Ser Met Ser Cys Thr Asp Phe Ser Phe His
                675                 680                 685
Phe Pro Val Cys Val Gln Asp Leu Ile Ser Pro Ile Asn Val Ser Leu
                690                 695                 700
Asn Phe Ser Leu Trp Glu Glu Glu Gly Thr Pro Arg Asp Gln Arg Ala
705                 710                 715                 720
Gln Gly Lys Asp Ile Pro Pro Ile Leu Arg Pro Ser Leu His Ser Glu
                725                 730                 735
Thr Trp Glu Ile Pro Phe Glu Lys Asn Cys Gly Glu Asp Lys Lys Cys
                740                 745                 750
Glu Ala Asn Leu Arg Val Ser Phe Ser Pro Ala Arg Ser Arg Ala Leu
                755                 760                 765
Arg Leu Thr Ala Phe Ala Ser Leu Ser Val Glu Leu Ser Leu Ser Asn
                770                 775                 780
Leu Glu Glu Asp Ala Tyr Trp Val Gln Leu Asp Leu His Phe Pro Pro
785                 790                 795                 800
Gly Leu Ser Phe Arg Lys Val Glu Met Leu Lys Pro His Ser Gln Ile
                805                 810                 815
Pro Val Ser Cys Glu Glu Leu Pro Glu Glu Ser Arg Leu Leu Ser Arg
                820                 825                 830
Ala Leu Ser Cys Asn Val Ser Ser Pro Ile Phe Lys Ala Gly His Ser
                835                 840                 845
Val Ala Leu Gln Met Met Phe Asn Thr Leu Val Asn Ser Ser Trp Gly
                850                 855                 860
Asp Ser Val Glu Leu His Ala Asn Val Thr Cys Asn Asn Glu Asp Ser
865                 870                 875                 880
Asp Leu Leu Glu Asp Asn Ser Ala Thr Thr Ile Ile Pro Ile Leu Tyr
                885                 890                 895
Pro Ile Asn Ile Leu Ile Gln Asp Gln Glu Asp Ser Thr Leu Tyr Val
                900                 905                 910
Ser Phe Thr Pro Lys Gly Pro Lys Ile His Gln Val Lys His Met Tyr
                915                 920                 925
```

```
Gln Val Arg Ile Gln Pro Ser Ile His Asp His Asn Ile Pro Thr Leu
    930             935             940

Glu Ala Val Val Gly Val Pro Gln Pro Pro Ser Glu Gly Pro Ile Thr
945             950             955             960

His Gln Trp Ser Val Gln Met Glu Pro Pro Val Pro Cys His Tyr Glu
            965             970             975

Asp Leu Glu Arg Leu Pro Asp Ala Ala Glu Pro Cys Leu Pro Gly Ala
            980             985             990

Leu Phe Arg Cys Pro Val Val Phe Arg Gln Glu Ile Leu Val Gln Val
        995             1000            1005

Ile Gly Thr Leu Glu Leu Val Gly Glu Ile Glu Ala Ser Ser Met
    1010            1015            1020

Phe Ser Leu Cys Ser Ser Leu Ser Ile Ser Phe Asn Ser Ser Lys
    1025            1030            1035

His Phe His Leu Tyr Gly Ser Asn Ala Ser Leu Ala Gln Val Val
    1040            1045            1050

Met Lys Val Asp Val Val Tyr Glu Lys Gln Met Leu Tyr Leu Tyr
    1055            1060            1065

Val Leu Ser Gly Ile Gly Gly Leu Leu Leu Leu Leu Leu Ile Phe
    1070            1075            1080

Ile Val Leu Tyr Lys Val Gly Phe Phe Lys Arg Asn Leu Lys Glu
    1085            1090            1095

Lys Met Glu Ala Gly Arg Gly Val Pro Asn Gly Ile Pro Ala Glu
    1100            1105            1110

Asp Ser Glu Gln Leu Ala Ser Gly Gln Glu Ala Gly Asp Pro Gly
    1115            1120            1125

Cys Leu Lys Pro Leu His Glu Lys Asp Ser Glu Ser Gly Gly Gly
    1130            1135            1140

Lys Asp
    1145
```